(12) United States Patent
Petyaev et al.

(10) Patent No.: US 11,224,234 B2
(45) Date of Patent: Jan. 18, 2022

(54) FUNCTIONAL CHOCOLATE

(71) Applicant: IMMD SP. Z.O.O., Warsaw (PL)

(72) Inventors: Ivan Petyaev, Cambridgeshire (GB); Marek Orlowski, Warsaw (PL)

(73) Assignee: IMMD SP. Z.O.O., Warsaw (PL)

( * ) Notice: Subject to any disclaimer, the term of this patent is extended or adjusted under 35 U.S.C. 154(b) by 0 days.

(21) Appl. No.: 16/348,641

(22) PCT Filed: Nov. 10, 2017

(86) PCT No.: PCT/EP2017/078918
§ 371 (c)(1),
(2) Date: May 9, 2019

(87) PCT Pub. No.: WO2018/087305
PCT Pub. Date: May 17, 2018

(65) Prior Publication Data
US 2020/0022381 A1    Jan. 23, 2020

(30) Foreign Application Priority Data

Nov. 10, 2016 (PL) .......................... 419423
Nov. 11, 2016 (GB) ..................... 1619044

(51) Int. Cl.
| | | |
|---|---|---|
| *A61K 36/73* | (2006.01) | |
| *A23G 1/42* | (2006.01) | |
| *A23L 33/105* | (2016.01) | |
| *A23G 1/48* | (2006.01) | |
| *A61K 31/065* | (2006.01) | |
| *A61K 36/185* | (2006.01) | |

(52) U.S. Cl.
CPC .............. *A23G 1/423* (2013.01); *A23G 1/48* (2013.01); *A23L 33/105* (2016.08); *A61K 31/065* (2013.01); *A61K 36/185* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 2008/0268097 A1 | 10/2008 | Hurst | |
| 2009/0110789 A1* | 4/2009 | Mower | A23L 2/52 426/330.5 |
| 2010/0254962 A1 | 10/2010 | Zehethofer | |
| 2011/0091637 A1* | 4/2011 | Abelyan | A23L 27/50 426/631 |
| 2011/0177174 A1 | 7/2011 | Crowley | |
| 2013/0280357 A1 | 10/2013 | Coy | |
| 2016/0095341 A1* | 4/2016 | Crozier | A23L 2/52 426/2 |
| 2020/0015505 A1* | 1/2020 | Prakash | A23L 27/36 |

FOREIGN PATENT DOCUMENTS

| | | |
|---|---|---|
| CN | 105494826 A | 4/2016 |
| CN | 105746824 A | 7/2016 |
| CN | 105767414 A | 7/2016 |
| CN | 105994867 A | 10/2016 |
| EP | 1508335 A1 | 2/2005 |
| EP | 2776464 B1 | 9/2016 |
| GB | 2452972 A | 3/2009 |
| KR | 20120118359 A | 10/2012 |
| KR | 20150087917 A | 7/2015 |
| WO | 2013029193 A1 | 3/2013 |
| WO | 2016007106 A2 | 1/2016 |

OTHER PUBLICATIONS

Petyaev, I. et al. Astaxanthin Co-Crystallized with Dark Chocolate Causes a Dose Dependent Inhibition of Oxidation Markers in Middle Aged Volunteers. American J of Food and Nutrition 6(5)153-158, 2018. (Year: 2018).*
Kozakiewicz, "Polyphenols—Meaning and Occurrence", https://www.poradnia.pl/polifenole-znaczenie-i-wystepowanie.html Apr. 24, 2016, English translation.
International Search Report and Written Opinion dated Mar. 23, 2018 for corresponding International Patent Application No. PCT/EP2017/078918.
Castro-Acosta et al., "Berries and anthocyanins: promising functional food ingredients with postprandial glycaemia-lowering effects." Proceedings of the Nutrition Society, Aug. 2016; 75, pp. 342-355.
Park et al., "A dose-response evaluation of freeze-dried strawberries independent of fiber content on metabolic indices in abdominally obese individuals with insulin resistance in a randomized, single-blinded, diet-controlled crossover trial."—Mol. Nutr. Food Res., May 2016; 60, pp. 1099-1109.
Li et al., "Purified anthocyanin supplementation reduces dyslipidemia, enhances antioxidant capacity, and prevents insulin resistance in diabetic patients." The Journal of Nutrition, Apr. 2015, 145, pp. 742-748.
Ramirez-Sanchez et al., "Epicatechin rich cocoa mediated modulation of oxidative stress regulators in skeletal muscle of heart failure and type 2 diabetes patients" Int J Cardiol. Oct. 9, 2013; 168(4), pp. 3982-3990.
Dorenkott et al., "Oligomeric cocoa procyanidins possess enhanced bioactivity compared to monomeric and polymeric cocoa procyanidins for preventing the development of obesity, insulin resistance, and impaired glucose tolerance during high-fat feeding." Journal of Agricultural and Food Chemistry, Mar. 12, 2014; 62; 2216-2227.

(Continued)

*Primary Examiner* — Ralph J Gitomer
(74) *Attorney, Agent, or Firm* — Tarolli, Sundheim, Covell & Tummino LLP

(57) ABSTRACT

This invention relates to consumable functional food comprising one or more cocoa bean products and a plant extract. The combination of a cocoa bean product and plant polyphenol have unexpected synergy leading to a significant health benefit. In addition, this invention describes unexpected synergy bioavailability and efficacy of polyphenol molecules of plant extracts, which they develop during fortification with them of consumable products where chocolate is a minor ingredient or not present at all.

13 Claims, 7 Drawing Sheets

(56) References Cited

OTHER PUBLICATIONS

Dilanka Fernando et al., "Extraction Kinetics of phytochemicals and antioxidant activity during black tea. (*Camellia sinensis* L.) brewing." Fernando and Soysa Nutrition Journal (2015) 14:74.

Petyaev et al., "Lycosome Formulation of Dark Chocolate Increases Absorption Cocoa Catechins and Augments Their Anti-Inflammatory and Antioxidant Properties." American Journal of Food Science and Nutrition, (2016) 3(3), pp. 37-44.

Brito et al., "Anthocyanin Characterization, Total Phenolic Quantification and Antioxidant Features of Some Chilean Edible Berry Extracts." Molecules 2014, 19, pp. 10936-10955.

Nakamura et al., "Development and Validation of a Liquid Chromatography Tandem Mass Spectrometry Method for Simultaneous Determination of Four Anthocyanins in Human Plasma after Black Currant Anthocyanins Ingestion." Journal of Agricultural and Food Chemistry, 2010, 58, pp. 1174-1179.

Postprandial Blood Glucose. American Diabetes Association. Apr. 2001, Diabetes Care, v. 24, No. 4, 775-778.

Johnston et al., "Dietary polyphenols decrease glucose uptake by human intestinal Caco-2 cells", FEBS Letters 579, (2005) pp. 1653-1657.

Dolinsky et al., "Calorie restriction and resveratrol in cardiovascular health and disease." Biochimica et Biophysica Acta. 1812, Nov. 2011, pp. 1477-1489.

Bonnefont-Rousselot, "Resveratrol and Cardiovascular Diseases", Nutrients 8, 250, May 2, 2016.

Bavaresco et al., "Wine Resveratrol: From the Ground Up." Nutrients 8, 222, Apr. 14, 2016.

"Limited time offer: Beauty chocolate, Chocolat du Aronia, enjoyable even during diet", Oct. 20, 2015 (online), pp. 1-3, retrieved on Aug. 27, 2021, retrieved from the internet: <https://www.j-cast.com/trend/2015/10/20248117.html.

\* cited by examiner

Comparison epicatechin MS spectra of aronia concentrate - solid line, and dark chocolate - dashed line.

A

B

C

FUNCTIONAL CHOCOLATE

FIELD OF THE INVENTION

This invention relates to consumable functional food comprising one or more cocoa bean products and a plant extract. The combination of a cocoa bean product and plant polyphenol have unexpected synergy leading to significant health benefits. This includes, but is not limited to, reducing or preventing a postprandial rise in blood glucose levels. The invention also relates to a milk chocolate with antioxidant, anti-inflammatory, anti-hypoxic and vascular supporting activity equivalent to dark chocolate. In addition, this invention describes unexpected synergy, bioavailability and efficacy of polyphenol molecules of plant extracts, which they develop during fortification of consumable products where chocolate is a minor ingredient. Also described are methods of making the consumable product with unexpected synergetic health benefits, and methods of reducing postprandial rises in blood glucose levels, as well as creating milk chocolate with antioxidant, anti-inflammatory, anti-hypoxic and vascular supporting activity equivalent to dark chocolate.

INTRODUCTION

Chocolate is a $100 bn dollar industry in the US, involving a range of products which are some of the most popular with consumers. More than 600 million people in the West alone consume these products. 85% of these people prefer milk chocolate (that is, chocolate products with less than 50% cocoa solids). Although it contains some beneficial nutrients, the overall consensus in the medical community is that milk chocolate may cause more harm than bring any health value. This is due to the fact that almost half of its mass is free sugar, which is considered to be one of the main causes of metabolic syndrome, diabetes and obesity. This is particularly applicable to milk chocolate, regardless of its cocoa content. Dark chocolate is healthier as it not only contains less sugar but is also richer in polyphenols which apart from other beneficial properties, may interfere with glucose absorption in the intestine, support insulin function and facilitate a more efficient utilisation of consumed glucose, resulting in more beneficial postprandial glucose profile. Dark chocolate contains catechins and epicatechins, which are reported to have beneficial effects on the cardiovascular system, mitochondria metabolism and epithelial metabolism.

Trans-resveratrol (3,5,4'-trihydroxy-trans-stilbene) (t-RSV) is a stilbenoid and a type of phenol that is produced naturally by a number of plants in response to biotic stress. t-RSV is typically present in red grapes, some berries, cocoa and nuts. There are a number of reported beneficial health effects of t-RSV from cardioprotective (see for example, Dolinsky et al. (2011), Bonnefont-Rousselot D et al., (2016) and Bavaresco L et al., (2016) incorporated herein by reference) to antidiabetic. However, one of its intriguing properties is the ability to activate a group of SIRT (Sirtuin) genes. These genes are responsible for controlling cellular stress protection and longevity.

When t-RSV is consumed as part of food, or as an isolated extract in the form of most supplements, it quickly becomes modified and inactivated in the digestive tract. Drinking red wine is the only known exception when t-RSV can reach the blood in an unmodified active form at a detectable level.

Accordingly, there is firstly a need to reduce the health implications associated with the consumption of chocolate, and in particular milk chocolate. For example, there is a need to reduce the rise in glucose levels observed following consumption of chocolate. It would furthermore be even more desirable for the consumption of chocolate to confer an additional health benefit. For example, it would be desirable to provide an alternative to red wine as a source of active t-RSV. The present invention addresses these needs.

The present invention also presents a new functional milk chocolate with epicatechins equivalent in their profile to dark chocolate and present in equal or higher levels than in dark chocolate. We also show that said polyphenol extract derived polyphenols need to be incorporated in the chocolate matrix in a proper, described manner to observe the benefits in postprandial glucose reduction, achieve epicatechins bioavailability and observe the epicatechins-related change in biomarkers of oxidative stress, inflammation and hypoxia that is comparable or higher than in dark chocolate.

Since milk chocolate indulgence appeals to a significantly broader consumer range than dark chocolate, this new functional consumable product would have significantly higher market reach, higher compliance and, because milk chocolate is cheaper than dark chocolate, a more affordable price, were its organoleptic qualities correspond more closely to those of milk chocolate than those of dark chocolate.

In addition, the core of this invention is an unexpected synergy in bioavailability and efficacy of polyphenol molecules of plant extracts when used to fortify consumable products, including food where chocolate is a minor ingredient.

SUMMARY OF THE INVENTION

According to a first aspect of the invention there is provided a consumable product comprising one or more cocoa bean products and a polyphenol-rich plant extract, wherein said consumable product comprises between 1 and 20%, preferably between 3 and 15% and more preferably between 5 and 10% or 9 and 11% of a plant extract. Preferably, the extract is a soft-solid, not dried and no free water polyphenol-rich plant extract. Accordingly, in one embodiment, the extract does not comprise free water and is not a dry powder. In a preferred embodiment, the extract is in a semi-solid state.

In one embodiment, said cocoa bean product comprises between 10 and 50%, more preferably between 15 and 40% cocoa butter and/or cocoa solid and said consumable product comprises between 1 and 20% polyphenol-rich plant extract, preferably between 3 and 15% and more preferably between 5 and 10% or 3 and 6% by weight of the total product. Preferably, said product comprises 37% cocoa butter and/or solids and optionally about 5% polyphenol-rich plant extract, by weight of the total product. Alternatively, said product comprises 20% or 25% cocoa solids. In a further embodiment, the cocoa bean product comprises at least 10% cocoa liquor and/or at least 10% cocoa butter and/or at least 25% cocoa solids. In one embodiment, the cocoa bean product is milk, white or dark chocolate.

In an alternative embodiment, said consumable product comprises between 9 and 11% polyphenol-rich plant extract by weight of the total product. Preferably, said consumable product comprises about 10% polyphenol-rich plant extract by weight of the total product. Preferably, said cocoa bean product comprises at least 50%, and more preferably between 50 and 99% cocoa butter and/or cocoa solid.

In one embodiment, the polyphenol is an amphiphilic and/or hydrophobic polyphenol. Preferably, the polyphenol is selected from the group comprising stilbenoids, catechins, epicatechins, gallocatechins, anthocyanins, anthocyanidins, curcumin, flavones, flavanols, flavanones, isoflavones, chalcones, phenolic acids and lignans. More preferably, the polyphenol is selected from a stilbenoid, anthocyanins, catechin and/or epicatechin. Preferably, the stilbenoid is resveratrol, and more preferably trans-resveratrol (t-RSV).

In one embodiment, the plant extract is or is derived from at least one of a group comprising berries, fruits, grapes, nuts, vegetables and grains. Preferably, the berry is selected from the group comprising *aronia* (or chokeberries), rowanberries, bilberries, blueberries, cranberries, blackcurrants, redcurrants, cherries, acai, apples, barberries, sea buckthorn and blackberries. More preferably, the berry is *aronia*, the fruit is the baobab fruit and the grain is buckwheat, or other members of the Fagorum family of plants, barley, wild or black rice.

In one embodiment, the consumable product comprises one or more additional agent, selected from the group comprising carotenoids, essential fatty acids, vitamins, whey protein prebiotics, probiotics or peptides, amino acids, minerals. Preferably, the carotenoid is lycopene. In a specific embodiment, the consumable product comprises between 0.05 and 0.30% lycopene, more preferably between 0.05 and 0.20% lycopene, even more preferably between 0.05 and 0.10% lycopene and most preferably 0.07% lycopene.

In one embodiment, the consumable product further comprises an extract or product of bacterial and/or fungal fermentation.

In a further embodiment, the cocoa bean product is cocoa butter and/or cocoa liquor and/or cocoa powder.

In another embodiment, the cocoa bean product is chocolate and accordingly, the consumable product is chocolate. In a preferred embodiment, the chocolate is milk chocolate and the consumable product comprises 5% *aronia* polyphenol-rich extract by weight of the total product. More preferably, the consumable product further comprises 0.07% lycopene by weight of the total product. Alternatively, the chocolate is dark chocolate and the consumable product comprises 10% *aronia* extract by weight of the total product. Preferably, the consumable product further comprises 0.07% lycopene by weight of the total product.

In another aspect of the invention there is provided a consumable product comprising one or more cocoa bean products and a polyphenol-rich plant extract, wherein said product comprises clusters of polyphenol-cocoa bean product crystals. Preferably, said product comprises at least 50% small clusters of the crystals, and/or up to 20% large clusters of polyphenol-cocoa bean product crystals.

In another aspect of the invention is a consumable product where chocolate is a minor ingredient, which is fortified with polyphenol rich plant extract resulting in an unexpected synergy in bioavailability and efficacy of polyphenol molecules of that extract.

In one embodiment, the plant extract is an *aronia* extract. In another embodiment, the consumable product is chocolate.

In another aspect, there is provided a method of producing a consumable product with antioxidant, anti-inflammatory, anti-hypoxic, vascular supporting and/or other health benefits, the method comprising combining a cocoa bean product with a polyphenol-rich plant extract. There is also provided a method of producing a consumable product that can reduce a postprandial rise in glucose levels, the method comprising combining a cocoa bean product with a polyphenol-rich plant extract, wherein preferably said consumable product is chocolate. In one embodiment, there is provided a method of producing a consumable product with reduced postprandial rise in glucose level when compared to unprocessed product.

In a further aspect, there is provided a method of preventing or reducing a postprandial rise in blood glucose levels, the method comprising administering a consumable product as described herein to a consumer or patient in need thereof. In one embodiment, the postprandial rise in blood glucose levels is reduced after the consumption of products containing chocolate, chocolate spread and chocolate and hazelnut spread.

In another aspect, there is provided a method of synergistically increasing the health beneficial properties or the health benefits of a cocoa bean product and plant polyphenols, which include but are not limited to antioxidant, anti-inflammatory, immune system modulation, vision support, anti-hypoxia and vascular supporting activity, the method comprising combining a cocoa bean product with a polyphenol-rich plant extract as described herein.

In yet another aspect, there is provided a method of increasing the level of at least one of resveratrol, catechins and another polyphenol(s) in blood serum, the method comprising administering a consumable product as described herein to a consumer or patient in need thereof. In one embodiment, there is provided a method of increasing the levels of epicatechin in blood serum, the method comprising administering a consumable product to a consumer or a patient in need thereof. Preferably the consumable product is milk chocolate. Preferably the level of resveratrol, catechins and another polyphenol(s) is increased to the level of or higher than the level observed in (standard, unmodified) milk or dark chocolate (of the same weight) or after ingestion of a consumable product comprising the same amount of a cocoa bean product (for example, a 10-15 g portion of chocolate or chocolate/hazelnut spread)). In another embodiment, there is provided a method of increasing resveratrol, preferably t-RSV, in blood serum, the method comprising administering a consumable product to a consumer or a patient in need thereof.

In a further aspect, there is provided a method of providing a dietary supplementation, preferably daily supplementation, of polyphenols, the method comprising administering a consumable product as described herein to a consumer or patient in need thereof.

In another aspect, there is provided a method for the treatment and/or prevention of a disorder selected from the group comprising metabolic syndrome, diabetes, inflammatory conditions, atherosclerosis, cancer, ocular disease, ageing of the skin bacterial and viral infections, and other tissues and pathologies of at least one of the cardiovascular system, nervous system, skeletomuscular system and liver, as well as cognitive impairment and healing processes impairments, the method comprising administering a consumable product as described herein to a patient in need thereof.

In a further aspect, there is provided a consumable product as defined herein for use as a medicament.

In another aspect, there is provided a consumable product as defined herein for use in the treatment and/or prevention of a disorder selected from metabolic syndrome, diabetes, inflammatory conditions, atherosclerosis, cancer, ocular disease, ageing of the skin, bacterial and viral infections and other tissues and pathologies of at least one of the cardiovascular system, nervous system, skeletomuscular system and liver, as well as cognitive impairment and healing processes impairments.

In a final aspect of the invention, there is provided the use of a consumable product as defined herein to provide a dietary supplement of polyphenol. Preferably said consumable product provides a daily supplement of polyphenols. More preferably, said consumable product is administered preferably daily to a consumer in need thereof.

The invention is further described in the following non-limiting figures.

FIGURES

Figure 3:
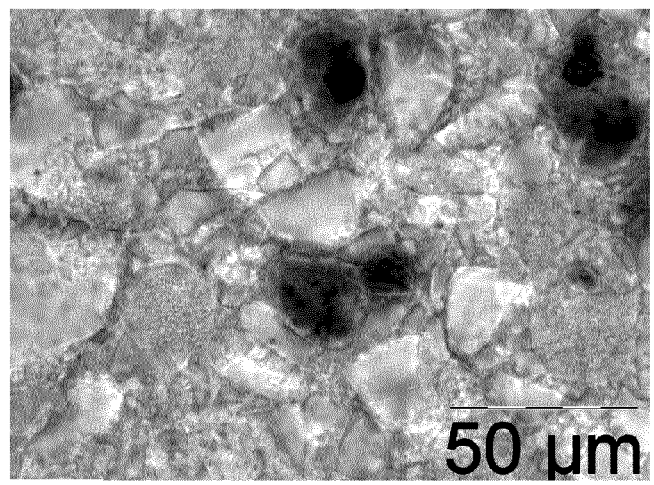
Figure 3:
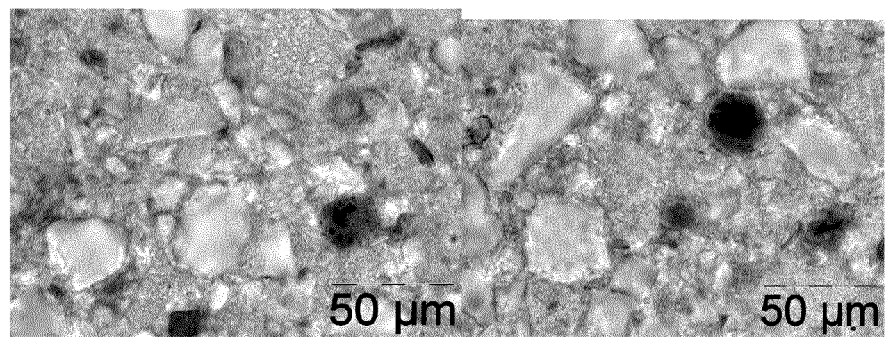
Figure 3:
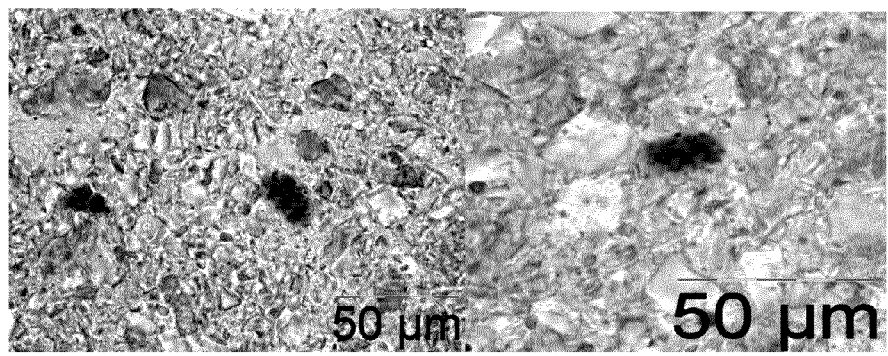

FIG. 3 shows chocolate crystals (also referred to herein as "poly-phenol-cocoa bean product crystals") embedded with blueberry anthocyanins and lycopene A: 500 mg blueberry extract+7 mg lycopene in White Chocolate; B: 500 mg blueberry extract+7 mg lycopene in Milk Chocolate; C: 500 mg blueberry extract+7 mg lycopene in Dark Chocolate.

Figure 4:
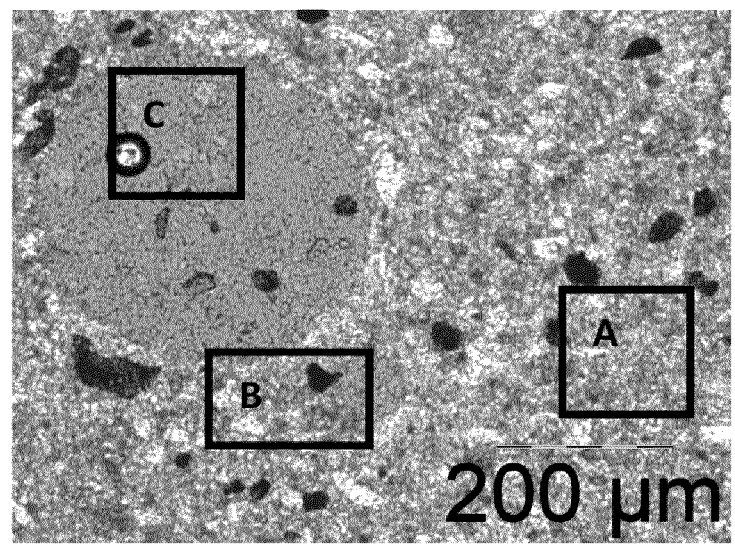

FIG. 4 shows crystals (poly-phenol-cocoa bean product crystals) of 85% Cocoa+500 mg *Aronia* extract. A—small clusters (or small poly-phenol-cocoa bean product crystals): <40 µm; B—medium size clusters (or medium poly-phenol-cocoa bean product crystals): 40-120 µm; and C—large clusters (or large poly-phenol-cocoa bean product crystals): >120 µm.

Figure 5:
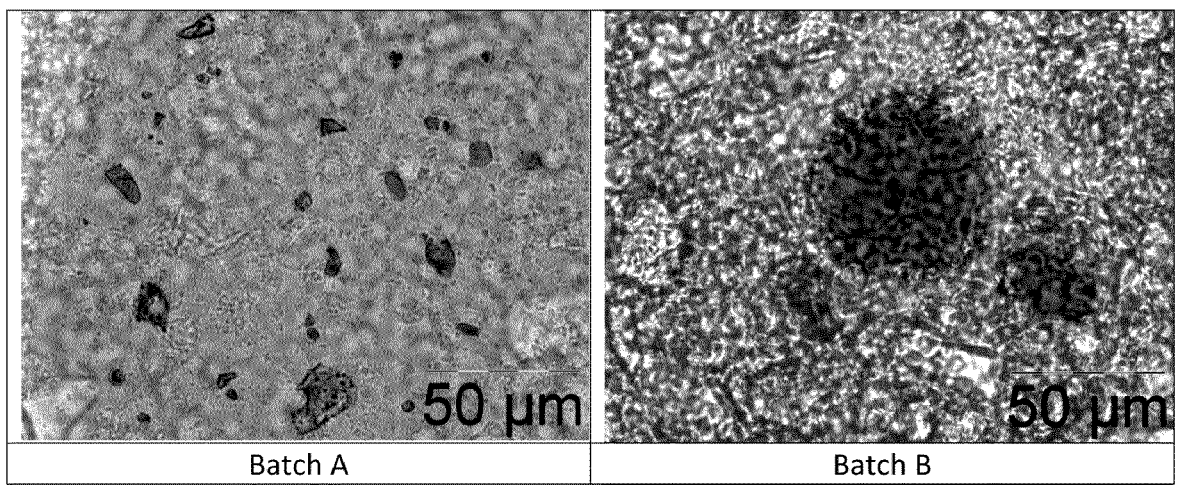

FIG. 5 shows microscopy images of two batches, A and B, of embedment of *aronia* extract into the dark chocolate matrix.

Figure 6:
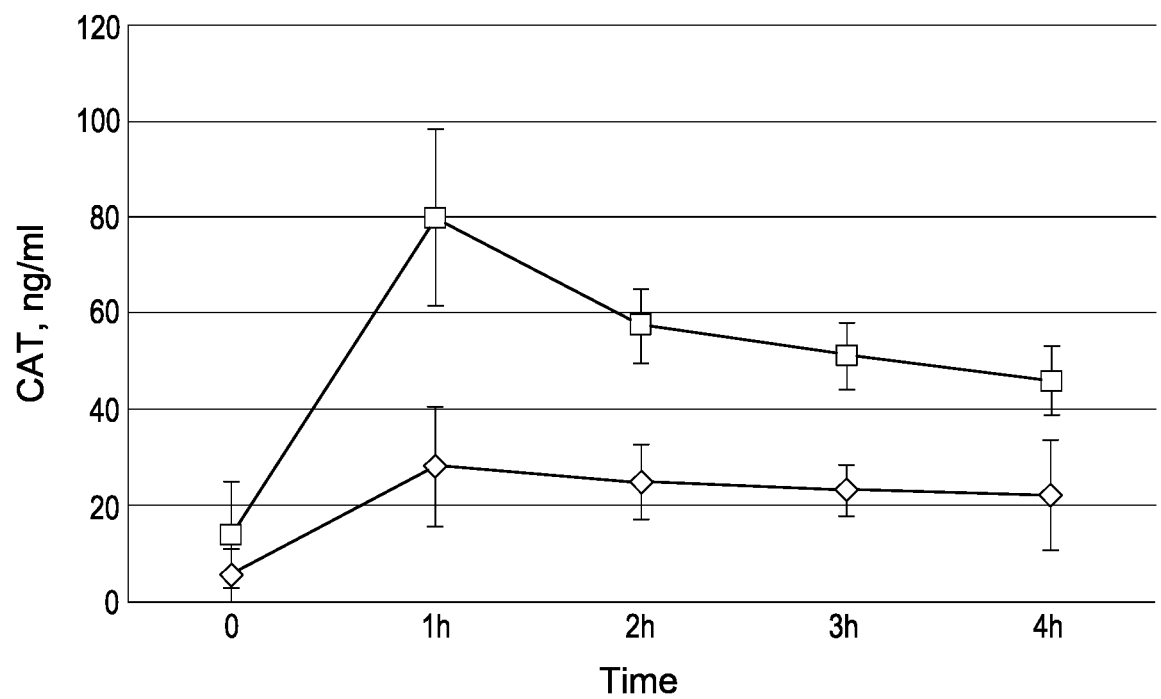

FIG. 6 shows an example of the synergetic boost of epicatechin metabolites by milk chocolate with *aronia* and coca polyphenol co-crystallisation. In particular, this figure shows a comparison of epicatechin metabolite pharmacokinetics of functional milk chocolate (i.e. a consumable product as described herein; cocoa 37%) with conventional dark chocolate (cocoa 50%) in a cross-over clinical study. Vertical axis is the concentration of the metabolites in the serum of the participants; horizontal axis is the time after ingestion of the chocolate samples; red—Lycotec functional milk chocolate; blue—dark chocolate. "CAT" is a combined concentration of "catechins", or actually epicatechins.

DETAILED DESCRIPTION OF THE INVENTION

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

The invention relates to the unexpected finding that certain plant extracts have unexpectedly high levels of polyphenols, and in particular, anthocyanins, flavanols (flavan-3-ol) such as catechin and epicatechin, and stilbenoids, such as resveratrol, and moreover, that these extracts can be surprisingly successfully combined with a cocoa bean product, such as chocolate to provide a number of significant health benefits. Specifically, it has been found that a consumable product comprising a cocoa bean product and a plant extract that is rich in anthocyanins and/or flavanols such as catechin and epicatechin, can be used to reduce or prevent postprandial rises in blood glucose levels, and can also increase the levels of catechins and/or epicatechins in the blood serum above the levels that would be observed after consuming the cocoa bean product alone. Of significant note, it has surprisingly been found that adding a fruit epicatechin rich extract to milk chocolate (as described in the product process below) creates a milk chocolate with equivalent or higher epicatechin postprandial levels and bioactivity to dark chocolate, when consumed in the same amounts. It has also been found that a consumable product comprising a cocoa bean product and a plant extract that is rich in stilbenoids, such as resveratrol, can be used to increase the levels of resveratrol in the blood serum above the level that would be observed after consuming either the cocoa bean product or plant extract alone or in combination as separate entities. In other words, the addition of a plant extract rich in resveratrol to a cocoa bean product has a synergistic effect on serum resveratrol levels.

Dark chocolate is generally known as healthy and bringing health benefits. The main benefits of dark chocolate come from its high content of cocoa solids. Cocoa (and especially cocoa solids) contain a high level of polyphenols, of which the most active and health-beneficial are catechins and epicatechins. However, dark chocolate, despite its health benefits, is sold in lower quantities than milk chocolate mostly due to:

1. high price; cocoa is expensive and its price has risen significantly over the last ten years;
2. taste; theobromine, some polyphenols and tannins are responsible for a bitter taste of high cocoa solids dark chocolate. Furthermore, cocoa carries other active compounds, apart from polyphenols, which are not necessarily tasty and sometimes can cause side effects, i.e. theobromine, can cause headaches; caffeine, can cause sleep problems and cardiovascular problems and histamine can contribute to immunological/allergies sensitivity and an inflammation-like state.

Also, due to above factors, dark chocolate is neither recommended nor preferred and appreciated by children, who stand for a significant share of chocolate users. In fact, the global market is dominated by milk chocolate, which stands for 85% of the market volume. However, milk chocolate does not carry the health benefits of dark chocolate due to:

1. lower level of cocoa solids (20-35% in most of the products vs 50-90% in dark chocolate);
2. milk additionally influences absorption of polyphenols in the intestine; and
3. milk chocolate contains more sugar than dark chocolate, which leads to postprandial glucose peaks.

Yet milk chocolate has two major commercial advantages over dark chocolate; it has better taste, demanded by both adults and children, and it is much cheaper than dark chocolate, which makes it more affordable.

As described herein, our invention provides a milk chocolate that is equivalent to dark chocolate (or actually is even better) with regard to epicatechin blood levels after consumption (as well as postprandial glucose levels). In particular, we provide;

A milk chocolate enhanced with fruit sourced polyphenols, in particular catechins that have an epicatechin efficacy profile equivalent to cocoa and dark chocolate. We also describe a milk chocolate that has a postprandial glucose profile equivalent to dark chocolate and significantly better (i.e. lower postprandial glucose peaks) than regular milk chocolate.

A milk chocolate with equivalent and better bioactivity than dark chocolate—in particular, with regard to its antioxidant effect on blood, tissues and lipoproteins. We also describe a milk chocolate that improves tissue oxygenation and reduces hypoxia.

A milk and dark chocolate enhanced with a fruit sourced extract that contains RSV. New unexpected findings show that RSV digested in the currently described form of dark and milk chocolate is significantly more bioavailable than when administered in a non-chocolate format.

A milk chocolate equivalent to dark chocolate in terms of polyphenols (e.g. epicatechins) content, bioavailability, bioactivity and glucose profile, but without the dark chocolate side effects and downsides i.e. cost, side effects, children use limitations, bitter taste.

A new milk and dark chocolate that enhances polyphenol bioavailability and has superior postprandial polyphenol blood level than regular chocolate.

A new milk and dark chocolate with reduced postprandial glucose peaks.

A new milk and dark chocolate that contains bioavailable anthocyanins.

New milk and dark chocolate pre-mixes that can be used in the production of any chocolate and confectionery chocolate containing product.

A new dark resveratrol chocolate that addresses consumer needs of a SIRT diet—for example, the present invention provides the benefits of red wine resveratrol) and dark chocolate (epicatechins) in a form of one 10-20 g bar of chocolate.

Milk and dark chocolate which has been confirmed to increase postprandial blood levels of resveratrol, anthocyanins and epicatechins to the levels unachievable for regular dark and particularly milk chocolate.

Chocolate based confectionery with health protective and disease preventive properties—such as, cardiovascular, cognition, oxidation stress, skin beauty, anti-aging, metabolic syndrome, obesity, pre-diabetes, muscle atrophy (sarcopenia), sports (performance, endurance, recovery), The invention is possible thanks to:

A new optimized method of chocolate tempering that leads to the formation of polyphenol containing crystals, which improve the bioavailability of the embedded polyphenols;

a method of crystal evaluation with regards to crystal size and number;

a fruits extract concentration method leading to the formation of a soft-solid, not dried and no free water, hydrogel of optimal viscosity and rheological parameters;

hydrogel form of extract concentration that is optimal for chocolate embedding. Regular liquid extract will not work due to water content, dry extract will not work due to taste/viscosity/smoothness/melting parameters (mouth melting experience is crucial for the chocolate quality perception and customer satisfaction);

a fruits soft-solid, not dried and no free water extract that has an epicatechins profile equivalent to cocoa and dark chocolate profile;

a method of said soft-solid, not dried and no free water hydrogel extract concentrate incorporation into a chocolate matrix leading to sustained palpable texture, smoothness, taste, melting properties and appropriate tempering process leading to crystals formation;

extensive data evaluating the pharmacokinetics of epicatechins, RSV and the bioactivity of the present consumable product and reference products;

effective inhibition of sugar/glucose absorption in the intestine, supposedly by the polyphenols action of the inhibition of glucose cell-transport system (as described in Johnston et al., (2005) for example);

unexpected effect of fruit polyphenols bioavailblity and bioactivity enhancement when embedded in our described chocolate (confirmed vs control regular extract).

In one aspect of the invention there is provided a consumable product comprising one or more cocoa bean products and a polyphenol-rich plant extract. In one embodiment, the cocoa bean product is chocolate. Accordingly, in one embodiment, the consumable product is chocolate (the term "chocolate of the invention" is also used and refers to chocolate supplemented with a plant polyphenol as described herein). Alternatively, the consumable product may comprise chocolate and a plant polyphenol as described herein. In other words, the consumable product may contain chocolate as an ingredient, but the consumable product is not, for example a chocolate bar.

In one embodiment, the consumable product comprises at least 1%, at least 2%, at least 3%, at least 4%, at least 5% or at least 10%, 15%, 20%, 25%, 30%, 35%, 40%, 45%, 50%, 55%, 60%, 65%, 70%, 75%, 80%, 85%, 90% or 95% by weight of a cocoa bean product. Surprisingly, we have identified that only very small percentages of cocoa bean product are required in the consumable product for the consumable product to have the above-described health benefits, and in particular only a small percentage of cocoa bean product is required for the consumable product to have the same health benefits of dark chocolate.

In one embodiment, the cocoa bean product is chocolate.

In another embodiment, the consumable product comprises at least 1%, at least 2%, at least 3%, at least 4%, at least 5% or at least 7%, 8%, 9%, 10%, 15%, 20%, 25%, 30%, 35%, 40%, 45%, 50%, 55%, 60%, 65%, 70%, 75%, 80%, 85%, 90% or 95% chocolate.

In one embodiment, there is provided a consumable product comprising a cocoa bean product and at least one polyphenol-rich plant extract, wherein said cocoa bean product comprises between 15 and 40% cocoa butter and/or cocoa solids and said consumable product comprises between 1 and 20% polyphenol-rich plant extract, more preferably 3 to 10% and even more preferably 3 to 6% or 5 to 10% polyphenol-rich plant extract, by weight of the total product. Preferably, the cocoa bean product comprises 37% cocoa butter and/or cocoa solids and about 5% polyphenol-rich plant extract, by weight of the total product. In a further embodiment, the consumable product comprises 20% or 25% cocoa solids or 10% cocoa liquor.

In a further embodiment, there is provided a consumable product comprising chocolate and between 1 and 20% polyphenol-rich plant extract, more preferably 3 to 10% and even more preferably 3 to 6% polyphenol-rich plant extract, by weight of the total product.

Preferably, the chocolate is milk, dark or white chocolate, and more preferably milk chocolate.

In another embodiment, there is provided a consumable product comprising chocolate and between 1 and 20% polyphenol-rich plant extract, more preferably 3 to 10% and even more preferably 5 to 10% polyphenol-rich plant extract, by weight of the total product. Preferably, the chocolate is milk, dark or white chocolate, and more preferably white chocolate.

In another embodiment there is provided a consumable product comprising one or more cocoa bean products and at least one polyphenol-rich plant extract, wherein said consumable product comprises between 9 and 11% polyphenol-rich plant extract by weight of the total product. Preferably said consumable product comprises about 10% polyphenol-rich plant extract by weight of the total product. More preferably, said cocoa bean product comprises between 50 and 99% cocoa butter and/or cocoa solids.

Accordingly, in a further embodiment, there is provided a consumable product comprising chocolate and between 9 and 11% polyphenol-rich plant extract by weight of the total product. Preferably, the chocolate is milk, dark or white chocolate, and more preferably dark chocolate.

For example, the consumable product may comprise between 1 and 1000 mg of the polyphenol-rich plant extract per gram of consumable product, for example, between 10 and 200 mg, or more preferably between 50 and 100 mg per one gram of consumable product.

In one embodiment, the product of the invention will typically provide an effective amount of the polyphenol-rich plant extract that is an amount that is effective to reduce a postprandial rise in blood glucose levels. Accordingly, in one embodiment there is provided a consumable product as described herein, wherein said product is capable of preventing or reducing a postprandial rise in blood glucose levels.

In another embodiment, the product of the invention will typically provide an effective amount of the polyphenol-rich plant extract is in an amount effective to increase the levels of a stilbenoid, such as resveratrol, in the blood serum. Accordingly, in one embodiment, there is provided a consumable product as described herein, wherein said product is capable of increasing the levels of a stilbenoid, such as resveratrol, in blood serum. In a further embodiment, the product of the invention will also typically provide an effective amount of the polyphenol-rich plant extract in an amount that is effective to increase the levels of a catechin and/or epicatechin and/or other polyphenol in the blood serum. Accordingly, in one embodiment, there is provided a consumable product as described herein, wherein said product is capable of increasing the levels of a catechin and/or epicatechin and/or other polyphenol in the blood serum.

The consumable product may comprise a homogenous matrix that contains the cocoa-bean products and the polyphenol-rich plant extract. In one embodiment, the cocoa-bean product and the polyphenol-rich plant extract may be blended together in a chocolate or cocoa-butter matrix.

A cocoa bean product is a product including an extract, fraction or isolate from cocoa beans (i.e. beans of the cacao tree (*Theobroma cacao*)). Suitable cocoa bean products are well-known in the art and include cocoa solid, cocoa liquor and/or cocoa butter. For example, a cocoa bean product may comprise one or more of cocoa solid, cocoa liquor and/or cocoa butter. In some instances the cocoa bean product may be cocoa nibs or fragments thereof, chocolate liquor, partially and fully-defatted cocoa solids (e.g. cocoa powder), cocoa extract or a fraction thereof.

Cocoa solid (also known as cocoa powder) is a low-fat extract of cocoa beans, which contains flavanols, flavanoids, caffeine and theobromine. Cocoa solid may be produced by removing the fat component (cocoa butter) from the cocoa bean and grinding the remaining material, excluding the shell, to a powder using techniques which are well-known in the art, such as Broma processing. In some embodiments, cocoa powder may be treated with an alkaline substance such as potassium carbonate to reduce acidity and darken the colour (Dutch processing).

Cocoa butter is a high-fat extract of cocoa beans which is high in stearic acid, palmitic acid and other saturated fats. Cocoa butter may be produced from whole or ground cocoa beans using techniques which are well-known in the art.

Cocoa liquor is a cocoa bean extract which contains both cocoa solid and cocoa butter. Cocoa liquor may be produced by grinding and melting the cocoa bean nib (centre) to a smooth liquid state in accordance with techniques which are well-known in the art. Chocolate liquor does not contain non-cocoa vegetable fat and may also be referred to as "chocolate", "unsweetened chocolate", "baking chocolate", or "bitter chocolate".

In other embodiments, cocoa bean products may include derivatives or fermentation products of cocoa bean extracts, isolates or fractions.

Preferably, the cocoa bean product comprises cocoa butter; cocoa solid; or both cocoa butter and cocoa solid. In one embodiment, the cocoa bean product is chocolate.

For example the cocoa bean product may contain at least 1% by weight, at least 10% by weight, at least 15% by weight, at least 20% by weight, at least 25% by weight or at least 30%, or at least 40% by weight cocoa butter. The cocoa bean product may contain an amount of cocoa butter in a range comprising any of the above two values as endpoints.

In some embodiments, a cocoa bean product or the consumable product may further comprise non-cocoa fats, such as vegetable or animal fats in addition to cocoa butter.

In some embodiments, a cocoa bean product may be devoid of cocoa butter. For example, a consumable product may contain animal or non-cocoa vegetable fat instead of cocoa butter. Non-cocoa vegetable fats may include vegetable oils. Suitable vegetable oils, such as palm oil, soybean oil rapeseed oil and olive oil, are well known in the art.

The total fat content of a cocoa bean product described herein may be at least 10% by dry weight, at least 15% by dry weight, at least 20% by dry weight, at least 25% by dry weight, at least 30% by dry weight or at least 35% by dry weight or at least 40% by dry weight. The fat content may be, for instance, in a range comprising any two such values as endpoints.

Additionally or alternatively, the cocoa bean product may contain at least 1%, 2%, 3%, 4% or 5% by weight, or at least 15% by weight, at least 20% by weight, at least 25% by weight, at least 30% by dry weight or at least 35% by weight, or at least 40% by weight dry cocoa solid. In some instances, the amount of cocoa solid may be at least 50% by weight, at least 60% by weight, at least 75% by weight, at least 80% by weight, at least 85% by weight, at least 90% by weight or even at least 95% by weight dry cocoa solid, particularly when the food stuff is a dark chocolate. The amount of weight of dry cocoa solid may be, for instance, in the range comprising any two of those values as endpoints.

In some embodiments, a consumable product may be devoid of cocoa solid.

For the avoidance of doubt, aspects of the invention provide cocoa bean products which comprise all combinations of the above parameters of cocoa solid, cocoa butter and total fat.

In some embodiments, the cocoa bean products may form a chocolate matrix. The polyphenol-rich plant extract may be incorporated into the chocolate matrix by blending or admixing. Therefore, in one embodiment there is provided a consumable product comprising chocolate and a polyphenol-rich plant extract. In this embodiment, the cocoa bean product is chocolate.

Any consumable product comprising a cocoa bean product may be supplemented with a polyphenol-rich plant extract as described herein. In one embodiment, the consumable product is a food. For example, the consumable product may be a foodstuff. In another embodiment, the consumable product is a beverage. Alternatively, the consumable product may be a dietary supplement or nutraceutical product.

Foodstuff products include bread, flour, cereal, biscuit, pastry, dairy products, such as cheese spread, cheese, cream and yoghurt, fillings, pastes, sauces and mousses, spreads, such as chocolate spreads, almond spreads and chocolate and hazelnut spreads (such as Nutella), chocolate pralines. Other suitable foodstuffs are well known in the art. In one embodiment, the foodstuff may comprise only a trace or small amount of cocoa bean product, and preferably comprise plant oil and/or ground hazelnut pulp.

In some preferred embodiments, foodstuff products may include confectionary products, such as chocolate or a chocolate-like product. Especially preferred embodiments of the invention provide chocolate comprising a polyphenol-rich plant extract, as described herein. In this embodiment, the consumable product is chocolate.

Chocolate may include dark chocolate, milk chocolate, or white chocolate.

In one preferred instance, the foodstuff of the invention may be a chocolate bar, for instance a dark, white or milk chocolate bar comprising a polyphenol-rich plant extract as discussed herein. The amount of polyphenol-rich plant extract in the bar, may be, for instance, any of the amounts of plant extract specified herein. Therefore, in another aspect of the invention there is provided a chocolate bar comprising a polyphenol-rich plant extract as described herein. In one embodiment, the chocolate may be white, milk or dark chocolate.

Accordingly, in one embodiment, there is provided a chocolate bar comprising 10 g of milk chocolate and between 3-6% of *aronia* extract. In an alternative embodiment there is provided a chocolate bar comprising 10 g of dark chocolate and 9 to 11% of *aronia* extract.

Dark chocolate, milk chocolate and white chocolate are subject to defined identity standards (for example, by the Food and Drug Administration (USA), EU and Food Standards Agency (UK); see for example EU directive 2000/36/EC; FDA 21 CFR Part 163 Federal Register: 2002 67 193 62171-62178). In one instance, a composition of the invention may be a standard of identity (SOI) chocolate, in others it is a non-SOI chocolate.

The ingredients of dark chocolate, milk chocolate, white chocolate or other forms of chocolate are well-known in the art.

For example, dark chocolate typically comprises sugar, cocoa butter (e.g. at least 12% by weight), cocoa solids (e.g. at least 35% or 50% by weight), and optionally vanilla. Fat content may vary but averages between 30%-35%. Dark chocolate is sometimes referred to as sweet or semi-sweet chocolate. In one embodiment, dark chocolate contains at least 50% cocoa solids.

Milk chocolate may comprise sugar, cocoa butter, cocoa solids, vanilla or other flavourings, and milk, milk powder or cream. Milk chocolate typically contains at least 20% or 25% cocoa solid and/or at least 12% milk solids by weight. In one embodiment, milk chocolate contains at least 10% chocolate liquor, which is a mixture of cocoa solids and fats (e.g. butter). In another embodiment, milk chocolate contains at least 20% cocoa solids. In a further embodiment, milk chocolate contains at least 25% cocoa solids.

White chocolate may comprise sugar, cocoa butter, milk or milk powder, and vanilla and lacks cocoa solids. White chocolate typically contains at least 20% cocoa butter, 14% total milk solids, and less than 55% sugar.

In one embodiment, the cocoa bean product contains palm oil instead of cocoa butter. Such products may be termed "chocolatey" or "with chocolate".

In a further embodiment, "milk" may refer to any type of milk, for example, dairy milk, or non-dairy milk such as almond milk, cocoa milk, rice milk and oat milk.

In one instance, the consumable product of the invention may be between 1 and 100 g, preferably between 1 and 50 g, even more preferably between 1 and 30 g, and most preferably around 10 g. Alternatively, the consumable product may be about 100 g, 150 g, 200 g, 250 g, 300 g, 400 g or 500 g in weight or may have a weight in a range with any two of those values as endpoints. In a preferred instance, the foodstuff may be a chocolate bar of such weight.

In another embodiment, the cocoa bean product and plant polyphenol extract may form a chocolate premix that is added to, used to coat or otherwise used in the production of any other foodstuff. Accordingly, in one embodiment, the consumable product is a chocolate premix.

The foodstuff may be a candy bar, for instance a chocolate coated candy bar. The foodstuff may take the form of individual chocolates, bagged chocolates or a box of chocolates. The chocolate may be in a formed shape. In one instance the foodstuff is an Easter egg. The invention may be provided in the form of chocolate icing or a cake comprising a polyphenol extract and chocolate. The invention also provides fruit or nuts coated with a chocolate of the invention. The invention also provides sweets or candy coated with a chocolate of the invention. The invention also provides ice-cream coated with a chocolate of the invention. In one embodiment, the amount of chocolate of the invention for coating is 10 to 15 g.

The invention also provides a chocolate of the invention provided in the form of a single serving dose, for instance in 5 to 50 g amounts, as well as a packet of such single serving doses. The invention also provides a chocolate bar of the invention segmented, for instance segmented so that it can be broken into single serving dosages. In one embodiment, the single serving dose may be between 1 and 100 g, preferably between 1 and 50 g, even more preferably between 1 and 30 g, and most preferably between 7 and 15 g. In one embodiment, the single serving dose is around 7.5, 10 g or 15 g.

The foodstuff of the invention may be, in other instances, chocolate incorporated into a cake, cheesecake, baked snack, brownie, cookie or biscuit, a meal replacement bar, a rice cake, ice cream or other pudding or dessert. In some instances, the invention provides such products coated in, or comprising, a chocolate of the invention. For example, the foodstuff may be a chocolate-coated wafer. The products may for instance comprise the chocolate in the form of chips or in a central region.

Dietary supplements or nutraceutical products may be in any form suitable for oral administration (e.g., by ingestion) and may be presented as discrete units such as capsules, cachets or tablets; as a powder or granules; as a solution or suspension in an aqueous or non-aqueous liquid; or as an oil-in-water liquid emulsion or a water-in-oil liquid emulsion; as a bolus; as an electuary; or as a paste, or as a chocolate bar, individually wrapped.

The invention also provides a food-stuff intended for dieters which is, or comprises, a foodstuff of the invention. The invention also provides for products for diabetics comprising, or consisting of, a foodstuff of the invention. In one instance, the invention provides a diabetic chocolate, where the chocolate is a chocolate of the invention.

In one preferred instance, a foodstuff of the invention may be provided with packaging and/or wrapping. Such packaging/wrapping may indicate the benefits of the invention and/or suggest consumption at, or near, mealtimes for maximal benefit. The packaging/wrapping may indicate the benefits of the product as described herein. In another instance, the packaging may refer to the ability of the product to decrease postprandial rises in glucose levels and/or increase bioavailable t-RSV, catechins and/or other polyphenol levels, preferably epicatechin and preferably postprandial levels. The packaging may refer to treating or ameliorating any of the conditions mentioned herein.

The consumable product may be produced by admixing or blending the cocoa-bean products, such as cocoa butter and cocoa solids, and optionally one or more other ingredients, and the polyphenol-rich plant extract under conditions which allow the polyphenol-rich plant extract to incorporate into the matrix of the consumable product.

Other ingredients in the consumable product may include at least one of sugar, vanilla, milk, milk powder, emulsifying agents, such as soy lecithin or polyglycerol polyricinoleate (PGPR; E476), whey or potato peptides and/or proteins, soy products, such as soy proteins, soy extracts and/or soy isoflavones, vegetable oils or animal fats, nut-based products, such as nut powders and nut extract, starch and polysaccharides. The milk powder may be cocoa milk powder, almond milk powder, rice milk powder or oat milk powder.

The cocoa-bean products may be in a dry, liquid, aerosol, frozen or melted form for admixing or blending with the polyphenol-rich plant extract. For example, chocolate for blending may be in liquid form (i.e. melted chocolate).

In some preferred embodiments, the cocoa-bean products and the polyphenol-rich plant extract are in mixable forms and have the same or similar viscosities.

Suitable methods of mixing and blending, including mechanical blending, are well-known in the art.

In one instance, the polyphenol-rich plant extract is added whilst the chocolate is being made or chocolate is melted and the polyphenol-rich plant extract added. The chocolate may be added to a mould to give products of a particular shape and/or size.

Products of the invention may also contain other ingredients such as flavourings, emulsifiers, colourings and/or preservatives. In some cases the products may comprise nuts, particularly where the product is a chocolate, such as walnuts, hazelnuts, almonds or brazil nuts.

A number of plants are known to contain high levels of polyphenols. Polyphenols are characterised by the presence of large multiples of phenol structural units. The number and characteristics of these phenol structures underlie the unique physical, chemical and biological properties of each member of the class.

Polyphenol compounds may have a broad range of solubility in water, from good to completely insoluble, with a molecular weight of 500-4000 Da, and with over 12 phenolic hydroxyl groups and with 7 aromatic rings per 1000 Da. The majority of polyphenols are however, hydrophobic and poorly water soluble. Alternatively, polyphenols may be defined as compounds exclusively derived from the shikimate/phenylpropanoid and/or the polyketide pathway, featuring more than one phenolic unit and deprived of nitrogen-based functions.

This invention relates to the unexpected finding that extracts from plants that are rich in polyphenols, and in particular, epicatechins, catechins and/or anthocyanins added to a cocoa bean product, are able to reduce or prevent postprandial rises in blood glucose levels, that would be expected following consumption of a cocoa bean product, such as a chocolate bar. The invention also relates to the unexpected finding that extracts from plants that are rich in polyphenols, stillbenoids, and in particular, resveratrol, specifically trans-resveratrol (t-RSV) added to a cocoa bean product can increase the levels of t-RSV, catechins and/or epicatechins and/or other polyphenols in blood serum, that would be expected following consumption of a cocoa bean product, such as a chocolate bar.

In one embodiment, the polyphenol is an amphiphilic and/or hydrophobic polyphenol. Preferably, the polyphenol is selected from the group comprising stilbenoids, catechins, epicatechins, gallocatechins, anthocyanins, anthocyanidins, proanthocyanidins, flavones, flavanols, flavanones, isoflavones, chalcones, phenolic acids and lignans or combinations thereof.

In one embodiment, the polyphenol is a stilbenoid. The stilbenoid may be selected from the group comprising piceatannolin, pinosylvin, pterostilbene, resveratrol, astringin and piceid. In a preferred embodiment, the stilbenoid is resveratrol, preferably t-RSV.

Resveratrol or 3,5,4'-trihydroxy-trans-stilbene, can be represented by the following structure:

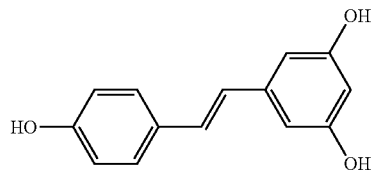 [SMILES: Oc1ccc(/C=C/c2cc(O)cc(O)c2)cc1]

In another embodiment, the polyphenol is anthocyanin, which can be represented by the following structure:

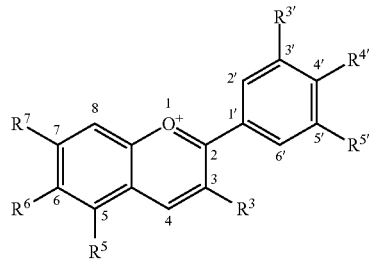

In a further embodiment, the polyphenol is a favan-3-ol (or flavanol). Preferably, the flavanol is catechin. Catechin has four diastereoisomers. Two of the isomers are in trans configuration and are called catechin and the other two are in cis configuration and are called epicatechin.

In one embodiment, the catechin is trans-catechin, i.e. catechin, and can be represented by the following structures:

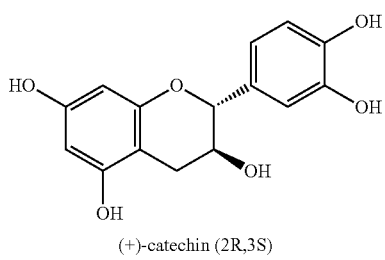

(+)-catechin (2R,3S)

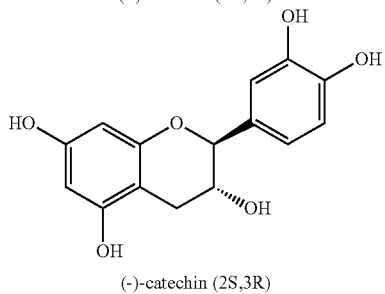

(-)-catechin (2S,3R)

Alternatively, the catehin is cis-catechin, i.e. epicatechin, and can be represented by the following structures:

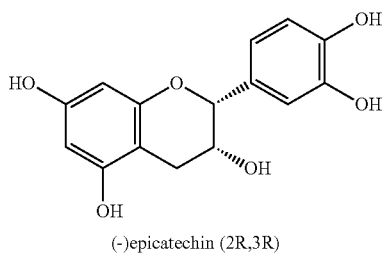

(-)epicatechin (2R,3R)

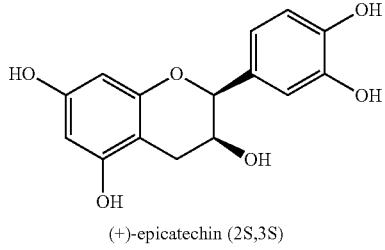

(+)-epicatechin (2S,3S)

Preferably, the polyphenol is t-RSV and/or epicatechin and/or catechin and/or anthocyanin or any combination thereof.

Plants that are rich in polyphenols can be readily identified by the skilled person using standard techniques in the art, for example, as described in Fernando & Soysa (2015), Petyaev et al, (2016), Brito et al. (2014), Nakamura et al., (2010) and Petyaev et al. (2011), which are incorporated herein by reference.

Once a plant has been identified as having a (preferably high) polyphenol content, the extract can be obtained using a number of techniques known in the art. The main objective of the extraction process used is to maximise extraction of amphiphilic and in particular hydrophobic polyphenols.

For this purposes a range of techniques can be used, for example use of ethanol, methanol and/or other organic solvents, supercritical $CO_2$, ultrasound pulsation, microwave-assisted, etc. Such techniques are well known to the skilled person.

Accordingly, in one embodiment, the soft-solid, not dried and no free water polyphenol-rich plant extract is obtained or obtainable by a method described above.

For extraction purposes we used the most rich polyphenol parts of the plant, which could be the fruits, berries, seeds, grains, or nuts, etc. For example, if fresh berries are used then, as the first step, the whole berries are immersed in ethanol-water solution, and then crushed and pressed, and left for incubation. This step can be repeated to maximise the level of extraction of the targeted polyphenols until a soft-solid, not dried and no free water extract is obtained.

Then the extracted solution gets separated from the remaining pulp of the berries.

For example, the soft-solid, not dried and no free water extract should contain either or in combination:
  trans-Resveratrol from 30-40 to 100 µg or more per 1 gram of the dry mass,
  catechins and epicatechins from 100 to 300 µg or more per 1 gram of the dry mass,
  anthocyanins 1-2 to 5 mg or more per 1 gram of the dry mass.

In one embodiment, the plant extract is or is derived from at least one of a berry, a fruit, a vegetable or grain. In a preferred embodiment, the berry is selected from, chokeberries (*Aronia* species (sp.)), rowanberries (*Sorbus aucuparia*), bilberries (*Vaccinium* sp. especially (*Vaccinium myrtillus*), blueberries (*Vaccinium* sp.), cranberries (*Vaccinium oxycoccos* or *Vaccinium macrocarpon*), blackcurrants (*Ribes* sp. especially, *Ribes nigrum*), redcurrants (*Ribes rubrum*), cherries (*Prunus* sp. such as *Prunus avium*), acai (*Euterpe* sp. such as *Euterpe oleracea*), barberry (or *berberis*), sea buckthorn (*Hippophae* sp.), grapes (such as members of *Vitis vinifera*) and blackberries (*Rubus* sp. such as *Rubus fruticosus*) or combinations thereof.

In a more preferred embodiment, the plant extract is a chokeberry extract, preferably an *aronia* extract. In one embodiment, the *aronia* extract is from a species of *Aronia* selected from the group comprising *Aronia arbutifolia*, *Aronia melanocarpa*, *Aronia prunifolia* and *Aronia mitschurinii* (also known as *Sorbaronia mitschurinii*). In a further preferred embodiment, the *aronia* extract is from the cultivar or variety *aronia* 3. Alternatively, the *aronia* extract is from the cultivar or variety *aronia* 5. In one embodiment, the *aronia* is Black chokeberry (also called *Aronia melanocarpa* or *Photinia melanocarpa*). In a further embodiment, the *aronia* extract is from the Viking, Autumn Magic or Nero variety, preferably the Nero variety of any of the above-described species.

In an alternative embodiment, the plant extract is a blueberry extract. Preferably, the blueberry extract is from a species of *Vaccinium* selected from the group comprising: *Vaccinium alaskaense* (Alaskan blueberry), *Vaccinium angustifolium* (lowbush blueberry), *Vaccinium boreale* (northern blueberry), *Vaccinium caesariense* (New Jersey blueberry), *Vaccinium corymbosum* (northern highbush blueberry), *Vaccinium constablaei* (hillside blueberry), *Vaccinium consanguineum* (Costa Rican blueberry), *Vaccinium darrowii* (evergreen blueberry), *Vaccinium elliottii* (Elliott blueberry), *Vaccinium formosum* (southern blueberry), *Vaccinium fuscatum* (black highbush blueberry; syn. *V. atrococcum*), *Vaccinium hirsutum* (hairy-fruited blueberry), *Vaccinium myrsinites* (shiny blueberry), *Vaccinium myrtilloides* (sour top, velvet leaf, or Canadian blueberry), *Vaccinium operium* (cyan-fruited blueberry), *Vaccinium pallidum* (dryland blueberry), *Vaccinium simulatum* (upland highbush blueberry), *Vaccinium tenellum* (southern blueberry), *Vaccinium virgatum* (rabbiteye blueberry; syn. *V. ashei*) *Vac-

*cinium koreanum, Vaccinium myrtillus* (bilberry or European blueberry) and *Vaccinium uliginosum*. In a further preferred embodiment, the blueberry extract is from cultivar Blue Gold 1 or Blue Gold 2, Aurora, Sportan, Chandler or Late Blue.

In an alternative embodiment the plant extract is or is derived from a fruit, preferably a baobab fruit extract. In one embodiment, the extract is from a member of the *Adansonia* genus, such as *Adansonia digitate, Adansonia grandidieri, Adansonia gregorii, Adansonia kilima, Adansonia madagascariensis, Adansonia perrieri, Adansonia rubrostipa, Adansonia suarezensis* and *Adansonia za*.

In a further alternative embodiment, the plant extract is a grain extract, wherein preferably the grain is buckwheat (*Fagopyrum esculentum*), barley (from the *Hordeum* species, such as (*Hordeum vulgare* L)), wild or black or brown rice.

By "polyphenol-rich plant extract" is meant a plant extract having a significant amount of at least one polyphenol described herein, such as stilbenoids, catechins, epicatechins, gallocatechins, anthocyanins, anthocyanidins, flavones, flavanols, flavanones, isoflavones, chalcones, phenolic acids, curcumin, chlorogenic acid and lignans.

In one embodiment, the plant extract may comprise between 0.05 and 12 mg/g of anthocyanin, more preferably, between 2 and 7 mg/g, and even more preferably between 2.3 and 5.6 mg/g of anthocyanin. In another embodiment, the plant extract may comprise between 50 µg and 1 mg/g of epicatechin and/or catechin, preferably, between 250 and 900 µg/g and even more preferably between 300 and 800 µg of epicatechin and/or catechin. In a preferred embodiment, the plant extract is a berry extract, preferably an *aronia* extract.

In another embodiment, the plant extract is a fruit extract and may comprise between 100 and 150 µg/g, more preferably between 130 and 145 µg/g of anthocyanins and/or between 600 and 17000 µg/g, more preferably between 16500 to 17000 µg/g (or 165 mg/g and 170 mg/g) of epicatechin and/or catechin. In a most preferred embodiment, the plant extract is a baobab fruit extract.

In another embodiment, the plant extract comprises between 25 and 150 µg/g of t-RSV. In one embodiment, the plant extract is preferably a blueberry extract and comprises between 30 and 120 µg/g of t-RSV, more preferably, between 34 and 106 µg/g. The plant extract may also preferably be a bilberry extract and comprise between 30 and 150 µg/g, more preferably between 36 and 100 µg/g of t-RSV. In another embodiment the plant extract is preferably an *aronia* extract and comprises between 30 and 150 µg/g, more preferably between 40 and 140 µg/g of t-RSV. In other embodiments, the plant extract may be a cherry extract and comprise between 40 and 60, preferably 50 to 55 µg/g of t-RSV, or the plant extract may be a barberry extract and comprise between 50-80 µg/g, preferably 60 to 75 µg/g of t-RSV.

In some embodiments, the plant extract may be a grain extract, such as buckwheat, and further comprise between 50 and 80 µg/g, more preferably between 60 and 65 µg/g of t-RSV.

In another embodiment of the invention, the consumable product may further comprise one or more additional agents. Such additional agents, may be selected from the group comprising carotenoids, essential fatty acids, vitamins, whey protein or peptides, amino acids, minerals and pre- or pro-biotics. Alternatively, the consumable product may further comprise an extract or product of bacterial and/or fungal fermentation.

In a preferred embodiment, the additional agent is a carotenoid. Carotenoid compounds are tetraterpenoids which contain long polyene chains. Carotenoid compounds include xanthophylls such as lutein, astaxanthin, capsanthin, meso-zeaxanthin and zeaxanthin, and carotenes, such as beta-carotene, alpha-carotene, zeto-carotene, and lycopene compounds. Preferably said carotenoid is lycopene.

Lycopene is an open-chain unsaturated $C_{40}$ carotenoid of structure I (Chemical Abstracts Service Registry Number 502-65-8).

Structure I

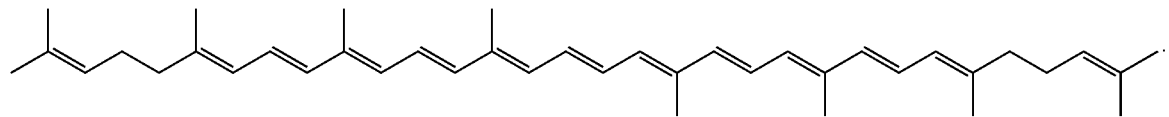

Lycopene
Molecular Weight = 536.89
Exact Mass = 536
Molecular Formula = C40H56
Molecular Composition = C 89.48% H 10.51%

Lycopene occurs naturally in plants such as tomatoes, guava, rosehip, watermelon and pink grapefruit and any such sources of lycopene may be, for instance, employed.

Lycopene compounds may include lycopene, 1-HO-3',4'-didehydrolycopene, 3,1'-(HO)2-gamma-carotene, 1,1'-(HO)2-3,4,3',4'-tetradehydrolycopene, 1,1'-(HO)2-3,4-didehydrolycopene.

Carotenoid compounds, such as lycopene, for use as described herein may be natural i.e. obtained from a natural source, for example, extracted from a plant, such as a tomato or melon. In one instance, oleoresin, particularly tomato oleoresin, may be employed in the invention. A range of methods for extracting, concentrating and/or purifying carotenoids from plants are known in the art. For example, solvent extraction using ethanol, DMSO, ethyl acetate, hexane, acetone, soya or other vegetable oil, or non-vegetable oils may be employed.

Carotenoid compounds, such as lycopene, for use as described herein may be synthetic i.e. produced by artificial means, for example, by chemical synthesis. A range of methods for chemical synthesis of lycopene and other carotenoids are known in the art. For example, a three-stage chemical synthesis based on the standard Wittig olefination reaction scheme for carotenoid synthesis may be employed, in which an organic solution of $C_{15}$ phosphonium methanesulfonate in dichloromethane (DCM) and an organic solution of $C_{10}$ dialdehyde in toluene are produced, and the two organic solutions are gradually combined with sodium methoxide solution and undergo a condensation reaction to form crude lycopene. The crude lycopene may then be purified using routine techniques, for example by adding glacial acetic acid and deionized water to the mixture, stirring vigorously, allowing the aqueous and organic phases to separate, and extracting the organic phase containing DCM and crude lycopene with water. Methanol is added to the organic phase and the DCM removed via distillation under reduced pressure. The crude methanolic lycopene solution is then heated and cooled to a crystalline slurry that is filtered and washed with methanol. The lycopene crystals may then be recrystalised and dried under heated nitrogen. Synthetic carotenoids, such as lycopene, are also available from commercial suppliers (e.g. BASF Corp, NJ USA).

Synthetic carotenoid compounds, such as lycopene, may comprise an increased proportion of cis isomers relative to natural carotenoid compounds. For example, synthetic lycopene may be up to 25% 5-cis, 1% 9-cis, 1% 13-cis, and 3% other cis isomers, whilst lycopene produced by tomatoes may be 3-5% 5-cis, 0-1% 9-cis, 1% 13-cis, and <1% other cis isomers. Since cis-lycopene has increased bioavailability relative to trans-lycopene, synthetic lycopene is preferred in some embodiments.

Derivatives of carotenoids as described above may be produced by chemical synthesis analogous to the synthesis described above or by chemical modification of natural carotenoids extracted from plant material.

A consumable product as described herein may contain a single carotenoid compound (e.g. lycopene) or more than one carotenoid compound (e.g. lycopene and beta-carotene). Typically, each carotenoid compound will be present in a range of different isomeric forms.

The consumable product may be produced by admixing or blending the cocoa-bean products, such as cocoa butter and/or cocoa solids, the polyphenol-rich plant extract and the carotenoid compound(s) under conditions which allow the carotenoid compound and the plant extract to incorporate into the matrix of the consumable product. In one embodiment, the consumable product comprises clusters of chocolate-polyphenol crystals. In a further embodiment, the cocoa bean product and the polyphenol-rich plant extract is further admixed or blended with at least one of palm oil, castor oil, or any other plant oil or fat.

In one embodiment, the consumable product comprises 0.1 to 1%, preferably, 0.05 to 0.08%, preferably 0.05, 0.06, 0.07 or 0.08% and most preferably 0.07% of carotenoid by weight of the total product. Alternatively, the consumable product comprises 0.1, 0.2, 0.3, 0.4, 0.5, 0.6, 0.7, 0.8, 0.9 or 1 mg, preferably 0.7 mg of carotenoid per gram of consumable product. In a preferred embodiment the carotenoid is lycopene.

In another aspect of the invention there is provided a method of producing a consumable product, such as a consumable product of the invention, which comprises adding a polyphenol-rich plant extract during production of the consumable product. There is provided a consumable product obtained or obtainable by the above described method.

The main objective of the presently described method of blending-in a plant extract into chocolate matrix is to cause specific co-crystallisation of plant polyphenols with chocolate crystals. This process is multivariable and the skilled person will understand that such method will need optimisation for every type, composition, recipe and manufacturing protocol of the chocolate. For example, a particular type of chocolate from a particular manufacturer has a particular composition, meaning a specific series of melting and tempering protocols is required. Every new batch must be assessed using microscopy to confirm the correct pattern, location and size of polyphenol embedment.

For example, where aronia extract is embedded into the Green & Black's® dark chocolate there are three main sizes of polyphenol clusters that can be identified (please see the microscopy image in FIG. 4).

From a series of different melting and tempering protocols and blending of the same dark chocolate with the same amount of aronia extract, from the same batch and in the same ratio, we selected two batches.

The first (A) contained 65% clusters with size more than 120 µm, and 10% below 40 µm. The chocolate in the second batch (B) contained 70% clusters with size below 40 µm, and 10% with size more than 120 µm. Typical microscopy images of these batches are presented in the FIG. 5.

One method of producing the consumable product of the invention is described below.

Example 1

Laboratory Production Method; Bilberry, or Blueberry or Aronia Polyphenol-Rich Extract and Milk Chocolate Co-Crystallisation This method describes the production of 1000 g Milk Chocolate dispensed as individual 10 g chocolates pieces each containing 500 mg of embedded bilberry, blueberry or aronia soft-solid, not dried and no free water polyphenol-rich extract (PRE).

Ingredients: 1000 g Green & Black's Organic 37% Cocoa Chocolate, 50 g of bilberry, blueberry or aronia PRE.

Ambient temperature in the production environment should be 20-21° C.

Warm the bulk stock of bilberry, blueberry or aronia PRE to a temperature of 40° C. and maintain at this temperature until required later.

Break off a single rectangular piece of chocolate approx. 25-30 g in weight. Store this piece of chocolate in a separate container until required later.

Break up the remainder of the 1000 g of chocolate into small pieces.

In a suitable container melt the chocolate to a temperature of 48° C.±1° C. Do not exceed this temperature during the melting process.

Stir the chocolate during the melting process.

When the chocolate appears to have melted completely stir thoroughly to ensure an even mixture with all chocolate melted.

Place the reserved 25-30 g piece of chocolate in an open container on a suitable balance, smooth surface of the chocolate uppermost. Set the balance to zero.

Take the bulk stock of bilberry, blueberry or aronia PRE from 40° C. incubation. Mix it thoroughly by rotation and inversion to ensure even mixing. Do not shake.

Carefully dispense 50 g of the bilberry, blueberry or aronia PRE on to the 25-30 g piece of chocolate by pouring.

Add the chocolate piece with the bilberry, blueberry or aronia PRE to the molten chocolate mixture at 48° C.±1° C.

Allow the chocolate piece to melt while stirring thoroughly to disperse the bilberry, blueberry or aronia PRE.

Once the chocolate piece has melted continue to stir the mixture and maintain a temperature of 48° C.±1° C. for a further 10 minutes then remove the heat.

Allow the mixture to cool to a temperature of 31° C. at an ambient temperature of 20-21° C. Stir the mixture as it cools.

When the mixture reaches a temperature of 31° C. begin to dispense 10 g quantities into suitable individual moulds by pouring.

Stir the mixture frequently during the dispense process to ensure even distribution of bilberry, blueberry or *aronia* PRE and dark chocolate co-crystallised clusters.

Maintain the mixture at a temperature of 29-31° C. during the dispense process by careful application of a small amount of heat.

Allow the individual 10 g chocolates to solidify at an ambient temperature of 20-21° C.

Each 10 g chocolate contains 500 mg bilberry, blueberry or *aronia* PRE and dark chocolate co-crystallised clusters.

Once solidified, store the chocolates away from light at 18-22° C. for wrapping.

Recommendations for Industrial Production

To guarantee stability:

bilberry, blueberry or *aronia* PRE embedment under:
1) restricted access of molecular oxygen, preferably under atmosphere of nitrogen or other inert gas
2) protection from light Sealed oxygen free (foil) packaging If this is not sufficient—use preservatives.

Quality Control

Guarantee certain size, density and uniformity throughout the chocolate mass with bilberry, blueberry or *aronia* PRE and dark chocolate co-crystallised clusters:

Microscopy—minimum formation of 70% clusters with size below 40 μm per 800μ$^2$ (×1,000), Mass Spectroscopy, HPLC and trans-Resveratrol antibody assay—to assess uniform distribution of epicatechins, anthocyanins trans-resveratrol.

As discussed above, the skilled person would understand that the process will need adjustment in line with the type of chocolate used.

Accordingly, in one embodiment, there is provided a method for the production of a consumable product, such as a consumable product of the invention, the method comprising:

Heating a polyphenol-rich plant extract, preferably to a temperature between 20 and 60° C., more preferably between 30 and 50° C., more preferably between 35 and 45° C., and most preferably 40° C.;

Dividing said cocoa-bean product into one more pieces or portions, preferably at least two pieces, wherein said pieces comprises a larger and smaller piece, and wherein preferably said smaller piece is at least 1%, at least 2%, at least 2.5%, at least 3%, at least 4%, at least 5%, at least 6%, at least 7%, at least 8%, at least 9% or at least 10% of the size of the larger piece. Preferably, said smaller piece is between 1 and 5%, preferably between 2 and 4% and even more preferably between 2.5 and 3% of the size of the larger piece;

Melting said larger piece of cocoa-bean product at a temperature of between 30 and 60° C., preferably between 40 and 50%, and eve more preferably at a temperature of 41° C., 42° C., 43° C., 44° C., 45° C., 46° C., 47° C., 48° C., 49° C. or 50° C. Even more preferably, melt the larger piece of cocoa bean product at a temperature of 48° C.;

Add the polyphenol-rich plant extract maintained at said temperature to said smaller piece of cocoa-bean product;

Add the polyphenol-rich plant extract-smaller piece of cocoa-bean product to said melted cocoa-bean product;

Melt said polyphenol-rich plant extract-smaller piece of cocoa-bean product in the already melted cocoa-bean product, to produce a mixture of cocoa-bean product and polyphenol-rich plant extract at a temperature of between 30 and 60° C., preferably between 40 and 50° C., and even more preferably at a temperature of 41° C., 42° C., 43° C., 44° C., 45° C., 46° C., 47° C., 48° C., 49° C. or 50° C. Even more preferably, melt the polyphenol-rich plant extract-smaller piece of cocoa-bean product at a temperature of 48° C.

Cool said mixture to at least a temperature of 50° C., more preferably 40° C. and even more preferably between 30 and 40° C., preferably 31° C., 32° C., 33° C., 34° C., 35° C., 36° C., 37° C., 38° C., 39° C. or 40° C.;

Optionally dispense the mixture into at least one individual mould, maintaining said temperature during dispending at at least 50° C., more preferably at least 40° C., more preferably at least 30° C., more preferably at least 20° C. In one embodiment, said temperature is maintained at between 20 and 30° C.

Optionally confirm the presence of polyphenol-chocolate crystals as described herein.

Accordingly, in a further aspect of the invention, there is provided a method of producing (preferably milk) chocolate with antioxidant, anti-inflammatory, anti-hypoxia, vascular supporting and other health beneficial activities on a par with dark chocolate, the method comprising the steps as described herein.

We also describe a method of polyphenol crystal embedment in a chocolate matrix (preferably milk, or white or dark chocolate) that involves procurement of the fruit polyphenol extract to its optimal viscosity and rheological parameters leading to optimal polyphenol crystal cluster formation in the chocolate matrix, optimal bioavailability of selected polyphenols in the form of chocolate embedded crystals and as a result optimal bioactivity of the polyphenols.

The results of a crossover study to assess the kinetics of postprandial glucose after ingestion of 10 g of either formulation (A) or (B) (as defined above) are presented in the Table 1 below.

TABLE 1

Effect of *aronia* polyphenol cluster profile in the dark chocolate on the postprandial glucose in the crossover clinical trial.

| | | Postprandial blood glucose, in mmol/L | | | | |
|---|---|---|---|---|---|---|
| Product, 10 g | n | baseline | 1 h | 2 h | 3 h | 4 h |
| Dark chocolate, Cocoa 85% control | 6 | 5.2 ± 0.3 | 6.0 ± 0.55 | 5.7 ± 0.5 | 5.5 ± 0.45 | 5.3 ± 0.35 |

TABLE 1-continued

Effect of *aronia* polyphenol cluster profile in the dark chocolate
on the postprandial glucose in the crossover clinical trial.

| Product, 10 g | n | Postprandial blood glucose, in mmol/L | | | | |
| --- | --- | --- | --- | --- | --- | --- |
| | | baseline | 1 h | 2 h | 3 h | 4 h |
| +500 mg *Aronia* (A) | 6 | 5.3 ± 0.5 | 6.2 ± 0.65 | 6.1 ± 0.55 | 5.8 ± 0.6 | 5.6 ± 0.5 |
| +500 mg *Aronia* (B) | 6 | 5.2 ± 0.45 | 5.9 ± 0.5 | 5.8 ± 0.55 | 5.6 ± 0.5 | 5.3 ± 0.4 |
| *Aronia* 500 mg* | 6 | 5.4 ± 0.45 | 6.1 ± 0.55 | 5.9 ± 0.5 | 5.7 ± 0.45 | 5.6 ± 0.5 |

*Aronia* extract capsule,

These results indicate that where large clusters of the *aronia* polyphenols are the dominating feature in the chocolate product, the rise of the postprandial glucose was significantly higher than when the same chocolate but *aronia* polyphenols were predominately embed in with smaller, more compact clusters.

Therefore, we decided to use the assessment of the size and the quantity of polyphenol clusters as a tool to optimise the embedment protocol and to provide new chocolate matrixes with the most synergetic outcome.

In another aspect of the invention there is provided a consumable product obtained or obtainable by the method described herein.

In another aspect of the invention there is provided a consumable product comprising one or more cocoa bean products and a poly-phenol-rich plant extract, wherein said product comprises clusters of polyphenol-chocolate crystals. Preferably the clusters can be of different sizes. As such these crystals can be classified as small, medium or large depending on their size. In one embodiment, small clusters are less than about 40 µm. In another embodiment medium clusters are between about 40 and 120 µm. In a further embodiment, large clusters are over about 120 µm in diameter. All measurements referred to herein in the context of are diameters.

In a preferred embodiment, the product comprises at least 50%, at least 60% and at least 70% or more preferably between 60 and 80%, large crystals, and/or up to 20%, preferably up to 10% small crystals. In an alternative embodiment, the product comprises at least 50%, at least 60%, at least 70%, at least 80%, at least 90%, more preferably at least 70% small crystals, that is crystals with a size less than 40 µm. In one embodiment, said product comprises said percentage of crystals per 800 µm² (preferably ×1000).

In another aspect of the invention there is provided a method of preventing or reducing a postprandial rise in blood glucose levels, the method comprising administering a consumable product as defined herein, preferably to a person or patient in need thereof. Alternatively, there is provided the use of a consumable product as defined herein to prevent or reduce a postprandial rise in blood glucose levels. In a preferred embodiment, the consumable product comprises a cocoa bean product and a poly-phenol rich plant extract wherein preferably the polyphenol is selected from anthocyanins, catechins and/or epicatechins.

Normally blood glucose levels rise after eating food that contains carbohydrate. This rise after food intake is a natural physiological process which is essential to supply our body with an energy source. However, particularly for people whose insulin system is already under stress and cannot effectively process this influx of glucose into the body, this postprandial rise in glucose levels can be problematic. For these people, the consumption of food, such as the consumable product described herein, which results in lower postprandial glucose are of significant benefit. For healthy individuals, the postprandial rise in glucose levels can also be problematic, leading to oxidative stress and inflammation, as well as a reactive insulin discharge, which may contribute in part to visceral obesity. Frequent glucose-insulin spikes can also lead to increased sugar cravings, which is why a low glycaemic index diet is recommended not only for pre-diabetic or diabetic individuals, but also for weight loss and weight management in healthy individuals. Reducing postprandial glucose spikes in confectionery products is therefore appealing to all consumers.

An increase in glucose levels to 6 nmol/L is considered harmful, and above this level, the insulin system is considered "stressed". We have found that the consumption of the product of the invention prevents or reduces this rise in blood glucose levels, and prevents a rise in blood glucose levels to above the harmful levels of 6 nmol/L or more.

Accordingly, in one embodiment, consumption of the consumable product of the invention prevents a rise in blood glucose levels above 6 nmol/L. In this context a reduction or prevention in the rise of glucose levels is relative to the levels observed following consumption of standard chocolate (such as milk or dark chocolate).

Accordingly, the product of the present invention is a healthier alternative to standard, commercially available chocolate, and can be used to control and/or reduce glucose intake by a consumer, and therefore prevent the potential health implications that can result from consumption of high levels of sugar, such as obesity, metabolic syndrome, non-alcoholic fatty liver disease (NAFLD), cardiovascular disease, cancer, diabetes and neurodegenerative disorders such as Alzheimer's disease. Moreover, the product of the present invention is particularly valuable for patients who are unable to physiologically control their blood sugar levels, such as diabetics.

In one embodiment, the product of the present invention is consumed under fasting or postprandial conditions. In another embodiment, the product prevents or reduces the rise in blood glucose levels that would normally be observed one hour after consumption of a sugar containing cocoa-bean product, such as a chocolate bar.

In one embodiment, the consumable product of the invention may be administered daily as a part of a healthy diet.

A "reduction" may comprise a reduction in the rise of postprandial blood glucose level by up to 50%, up to 40%, 30%, up to 20%, up to 15%, up to 10%, 9%, 8%, 7%, 6%, 5%, 4%, 3%, 2% or 1% compared to the postprandial rise observed after consumption of a cocoa-bean product without the polyphenol-rich plant extract. A "prevention" may comprise no change or no statistically significant change in the blood glucose level from before and after consumption of the product of the invention. In one embodiment "after" consumption may be anytime up to three hours, preferably, two, and even more preferably up to and including one hour following consumption. In a specific embodiment, consumption of the consumable product reduces postprandial glucose levels 20 mins, 30 minutes, 40 minutes, 50 minutes or at one hour following consumption.

Methods of measuring levels of postprandial glucose levels are well known in the art. (please see for example, Postprandial Blood Glucose (2001), incorporated herein by reference).

In a further aspect of the invention there is provided a method of increasing the level of at least one of resveratrol, preferably t-RSV, catechins, epicatechins and other polyphenols in blood serum, the method comprising administering a consumable product as defined herein, preferably to a person or patient in need thereof. Alternatively, there is also provided the use of a consumable product as defined herein to increase the levels of t-RSV, catechins, epicatechins and/or other polyphenols in blood serum. In a preferred embodiment, the consumable product comprises a cocoa bean product and a poly-phenol rich plant extract wherein the polyphenol is a stilbenoid, preferably resveratrol, more preferably t-RSV. In another embodiment, the polyphenol is selected from catechins epicatechins and/or other polyphenols.

In one embodiment, the level of t-RSV, catechins, epicatechins and/or other polyphenols is increased relative to the levels observed following administration of the cocoa bean product or the plant extract alone. Accordingly, in one embodiment the cocoa bean product and plant extract are present in a synergistic amount. In other words, the combination of a plant extract as described herein and a cocoa bean product produces a greater effect on the level of t-RSV, catechins, epicatechins and/or other polyphenols in blood serum than either individually when provided in the same amount. In another embodiment, the level of t-RSV in blood serum is equivalent to that observed following consumption of 350 ml of red wine. In another embodiment, the level of catechins, epicatechins and/or other polyphenols is equivalent to or higher than that observed following consumption of a cocoa-bean product alone, such as (standard, unmodified) chocolate, preferably dark chocolate.

An "increase" in t-RSV, catechins, epicatechins and/or other polyphenols levels may comprise an increase of at least 1-fold, 2-fold, 2.5-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold or 20-fold, compared to the levels observed following consumption of the cocoa bean product alone. Preferably, the levels are increased at least 6-fold, more preferably 8 fold, and even more preferably 10-fold.

In a specific embodiment, administration of the consumable product of the invention may result in a maximum serum level of t-RSV between 50 and 250 ng/ml, more preferably between 80 and 200 ng/ml, and in one embodiment, between 140 and 190 ng/ml, even more preferably between 140 and 180 ng/ml. Preferably the plant extract is an *aronia* extract.

In one embodiment, the increase in t-RSV, catechins, epicatechins and/or other polyphenols levels are observed at least one, two, three, four or five hours following administration of the consumable product described herein.

As described herein, consumption of the consumable product of the invention results in an increase in not only t-RSV in blood serum levels, but the levels of unmodified and/or active t-RSV. There are number of metabolites of t-RSV which are produced by the human gut flora or the bodies' own enzymes. Most of these are sulphates and glucuronides and they are typically detected in blood and or urine. The biological activity of these metabolites, however, remains unknown. However, detection of unmodified t-RSV in the blood unequivocally indicates that the powerful molecule with well-established biological activity is already in circulation. Accordingly, in one embodiment, "active" t-RSV refers to an unmodified or a form of t-RSV that has not been metabolised by the gut flora or the bodies' own enzymes.

Accordingly, in one embodiment, the method described herein increases the levels of bioavailable t-RSV, catechins, epicatechins and/or other polyphenols. By "bioavailable" is meant the fraction of an administered dose of bioactive molecules such as t-RSV, catechins, epicatechins and/or other polyphenols that reach the systemic circulation unchanged. In one embodiment, the methods of the present invention increase the levels of bioavailable t-RSV, catechins, epicatechins and/or other polyphenols up to 5-fold, 6-fold, 7-fold, 8-old, 9-fold, 10-fold, 11-fold, 12-fold, 13-fold, 14-fold, 15-fold, 16-fold, 17-fold, 18-fold, 19-fold or 20-fold, compared to the amount of bioavailable t-RSV catechins, epicatechins and/or other polyphenols obtained following consumption of a cocoa bean product alone. In a preferred embodiment, the method described herein increases the levels of bioavailable epicatechins.

In another aspect of the invention there is provided a consumable product as described herein for use as a medicament. Alternatively, there is provided the use of a consumable product as described herein in the preparation of a medicament for use in the treatment and/or prevention of a disease.

In a further aspect of the invention there is provided a consumable product for use in the treatment and/or prevention of a disorder selected from diabetes, an inflammatory condition, atherosclerosis, cancer, ocular disease, a metabolic syndrome, ageing of the skin, bacterial and viral infections and pathologies of the cardiovascular system, nervous system, skeletomuscular system or liver. Alternatively, there is provided the use of a consumable product of the present invention in the preparation of a medicament for the treatment and/or prevention of a disorder selected from diabetes, an inflammatory condition, atherosclerosis, cancer, ocular disease, a metabolic syndrome and ageing of the skin, bacterial and viral infections and pathologies cardiovascular system, nervous system, skeletomuscular system or liver. In one embodiment, the disorder may be selected from metabolic syndrome, diabetes, an inflammatory condition, atherosclerosis, cancer, ocular disease, a metabolic syndrome and ageing of the skin and other tissues and pathologies of cardiovascular system, nervous system, skeletomuscular system or liver.

In another aspect of the invention there is provided a method for the treatment and/or prevention of a disorder selected from diabetes, an inflammatory condition, atherosclerosis, cancer, ocular disease, a metabolic syndrome and ageing of the skin, bacterial and viral infections and pathologies of the cardiovascular system, nervous system, skeletomuscular system or liver, the method comprising administering the consumable product of the invention to a patient in need thereof.

An inflammatory condition may include both sub-clinical and clinically manifested inflammation. It may also include accidental or intentional trauma or damage to organs and tissues, like accidents or operations. It may also include pathological conditions and diseases. This may include chronic and acute infections, arthritis, auto-immune pathologies, etc. An inflammatory component is one of the main contributors of body disease processes regardless of the organ or tissue, from heart and vasculature system to the brain and eye, from the liver and pancreas to reproductive and hormonal system, from skeletal muscle and bones to haematopoiesis, from lungs to gastrointestinal system, etc.

An individual is preferably a human, though use in animals is also possible. The individual may have normal blood levels of glucose. In some embodiments, the individual may be at suffering from, or at risk of suffering from a disorder selected from pre-diabetes, diabetes, obesity, an inflammatory condition, atherosclerosis, cancer, ocular disease, a metabolic syndrome and ageing of the skin, bacterial and viral infections, cardiovascular system, nervous system, skeletomuscular system or liver. In some embodiments, a suitable individual may be a mature or elderly individual, for example at least 50, 60, 65, 70, 75 or more years old or be of an age in the range defined by any of those two values.

The consumable product described herein is found to reduce levels of markers of both inflammation and inflammatory oxidative damage in an individual. In some cases the subject may have elevated levels of inflammatory oxidative damage.

Accordingly, in one embodiment, there is provided a method of reducing the levels of oxidative and/or inflammatory damage markers in an individual, the method comprising administering the consumable product of the present invention to an individual in need thereof. In one embodiment, the level of oxidative and/or inflammatory damage markers is reduced after two, three or four weeks following daily administration of the consumable product.

Another aspect of the invention provides a nutraceutical, a nutracosmetic or nutricosmetic formulation comprising one or more cocoa bean products and a polyphenol-rich plant extract, as described herein.

A nutraceutical, nutracosmetic or nutricosmetic formulation which comprises one or more cocoa bean products and a polyphenol-rich plant extract as defined above, and may further comprise one or more cosmetically or nutritionally acceptable carriers, adjuvants, excipients, sweeteners, diluents, fillers, buffers, stabilisers, preservatives, colourings, lubricants, or other materials well known to those skilled in the art.

The term "nutraceutically acceptable" or "nutricosmetically acceptable" as used herein pertains to compounds, materials, compositions, and/or dosage forms which are in common or widespread usage in food and dietary products and are generally considered non-toxic, for example, compounds may have the US FDA designation "GRAS" (Generally Recognised as Safe), or equivalent food additive status in other jurisdictions.

Nutraceutic, nutracosmetic or nutriceutic formulations are generally intended for oral administration and may be formulated accordingly. Nutracosmetic or nutricosmetic formulations may be useful in improving the appearance of an individual or in reducing, delaying or masking visual signs of aging in an individual.

The invention may therefore be administered to treat, ameliorate, prevent, or reduce the severity of symptoms in any of the conditions referred to herein. In one instance, the invention is administered prophylactically to help prevent the onset of any of the conditions mentioned herein. The invention may result in reduction of any of the parameters discussed herein, it may, for instance, reduce postprandial rises in glucose levels.

A final aspect of the invention provides a consumable product comprising at least one cocoa bean product and a polyphenol compound, wherein said polyphenol is selected from the group comprising or consisting of anthocyanins, epicatechins, catechins and/or t-RSV, or combinations thereof.

In one embodiment, the consumable product comprises between 100 and 150 µg/g, more preferably between 130 and 145 µg/g of anthocyanins.

In another embodiment, the consumable product comprises between 10 µg and 800 µg/g of epicatechin and/or catechin, preferably, between 10 and 40 µg/g and even more preferably between 300 and 800 µg of epicatechin and/or catechin.

Alternatively, the consumable product may comprise between 25 and 150 µg/g of t-RSV, preferably between 30 and 120 µg/g of t-RSV. In one embodiment, the consumable product comprises between 34 and 106 µg/g t-RSV. In another embodiment the consumable product comprises between 30 and 150 µg/g, more preferably between 40 and 140 µg/g of t-RSV. In a specific embodiment, the consumable product comprises between 2.5 and 4.0 µg/g, and even more preferably 2.5 to 3.5, or 2.9 to 3.0 µg/g of t-RSV.

The polyphenols described in this embodiment may be synthetic, i.e. produced by artificial means, such as chemical synthesis. A range of methods for the production of the above-described polyphenols and polyphenol-rich extracts and products are known in the art. Alternatively, the polyphenols described above may be derived from natural sources, such as from plant extracts. In one embodiment, the polyphenols are derived from plants such as berries, fruits, grapes, vegetables and grains. Examples of suitable berries, fruits, grapes, vegetables and grains are described above.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

EXAMPLES

1. The Source of the Polyphenols for Chocolate Fortification

For this purpose we decided to fortify chocolate with the same type of insulin supporting polyphenol that are present in cocoa, anthocyanins and the same forms of catechins. While it is possible to obtain polyphenol extracts from cocoa this has at least two main drawbacks—sustainability of this source and its cost. In addition, the "clutching" process used to produce current chocolates significantly reduces the level of polyphenols present originally in cocoa.

To circumvent this problem we screened a number of plant sources, obtained extracts and analysed them with a focus on anthocyanins and the catechins/epicatechins in a form similar, or identical, to the cacao ones, and which are known to be beneficial to insulin metabolism (Castro-Acosta M L et al., (2016), Park E et al., (2016), Li D et al., (2015), Ramirez-Sanchez I et al. (2013) and Dorenkott M R et al. (2014)).

Results of this work are presented in Table 2. As a result of industrial processing dark chocolate contains significantly lower levels of catechins (and some other polyphenols) than in the raw cocoa. Since all the accumulated and published evidence on the health benefits of cocoa were obtained in trials where dark chocolate and not the cocoa raw material was consumed, we decided to use chocolate as our reference product.

The results presented in Table 3 demonstrate that some European plants are a good source of catechins, such as buckwheat and bilberry. However, the highest concentration among this group was *aronia*. The overall unexpected "champion" in the catechin content was the fruit of the African tree baobab, the concentration of which was even 2.5 times higher than in the raw cocoa bean.

In terms of anthocyanin the highest concentration was detected in three berries—blueberries, bilberries and *aronia*.

TABLE 2

| | Epi- & Catechins | | Anthocyanins | |
|---|---|---|---|---|
| Products | Literature | Our data | Literature | Our data |
| Cocoa bean powder | | | | |
| West Africa | | 6,385 μg/g | | 0.62 mg/g |
| Cocoa nibs or cotyledons | | 3,135 μg/g | | 0.12 mg/g |
| Dark chocolate | | | | |
| Cocoa 70-75% | 478-515-605 μg/g | 717 μg/g | 0.16-0.36 mg/g | |
| Blueberry | | | | |
| Poland | 1.24 mg/g | 175 μg/g | 0.64-1.38-1.63 mg/g | 0.09-9.5 mg/g |
| | | 16 mg/L | | 1.4 mg/g |
| | | | | 308 mg/L |
| Czech Republic | | 92.8 μg/g | | |
| Bilberry | | 271 μg/g | 1.5-2.85-6.4 mg/g | 3.3-7.9 mg/g |
| | | 24 mg/L | | 297-409 mg/L |
| Aronia | 145 μg/g | 308-795 μg/g | 1.48-1.96-3.5-4.3 mg/g | 2.3-5.6 mg/g |
| | | 33-73 mg/L | | 230-454 mg/L |
| Red wine | 22-103-168-184 μg/g | | 0.36-1.53 mg/g | |
| | | | 80-177 mg/L | |
| Grape | | | | |
| Red | 20 μg/g | | 0.48-1.2 mg/g | |
| California | | 22.5 μg/g | | 0 μg/g |
| Chile | | 32.4 μg/g | | 0 μg/g |
| Greece | | 29.2 μg/g | | 14.7 μg/g |
| Australia | | 49.1 μg/g | | 0 μg/g |
| White | | | | |
| South Africa | | 342 μg/g | | 0 |
| Australia | | 89.9 μg/g | | 0.32 μg/g |
| Cherry Morello | 41.3-53.9 μg/g | 133 μg/g | 134-345 μg/g | 343 μg/g |
| Acai | | 260 μg/g | | 6.1 mg/g |
| Barberry | | 75.2 μg/g | | 230 μg/g |
| Goji | | 18.9 μg/g | | 0 μg/g |
| Mulberry | | 12 μg/g | | 1.1 mg/g |
| Sea Buckthorn | | 100 μg/g | | 0 μg/g |
| Baobab | | | | |
| Ghana | n/a | 665 μg/g | | 139 μg/g |
| n/i blend | | 2,340 μg/g | | 36.7 μg/g |
| Malawi | | 16,823 μg/g | | 0.8 μg/g |
| Hemp | | 1.59 μg/g | | 23.4 μg/g |
| Barley | | 139 μg/g | | 0 |
| Aubergine | | | | |
| raw | | 0 | | 6.7 μg/g |
| dried | | 0.15 μg/g | | 81.8 μg/g |
| Flaxseed | | 0 | | 514 μg/g |
| Buckwheat | | 234 μg/g | | 90.2 μg/g |

Comparison of the concentration of catechins and anthocyanins in extracts of cocoa products and different plants While working with different sources of even the same berries we realised that the concentration of these polyphenols was significantly variable, even between cultivars.

As presented in Tables 3 and 4, the content of catechins in one cultivar of blueberries, Blue Gold, was significantly, up to 100 fold, higher than in many other varieties. This same variability for another critical group of polyphenols, anthocyanins and anthocyanidins, was also observed for different cultivars, as shown in Table 4.

This unpredictability of the polyphenol concentrations was observed for a range of plants—baobab (Table 2), bilberries (data not presented) and *aronia* varieties even growing in the same country (Table 5).

This indicates that the mere use of a blueberry, or *aronia*, or any other source to obtain extracts sufficiently rich with catechins, or anthocyanins, or maybe other polyphenols may not be suitable for the creation of functional milk chocolate, or any other form of chocolate, that is equivalent to dark chocolate (in terms of the above described health benefits).

TABLE 3

Catechin, methylxanthine and bioamine concentrations in different blueberry cultivars.

| Blueberry Cultivar | Bioactive molecules per mg/g | | | | |
|---|---|---|---|---|---|
| | Catechins & epicatechins | Caffeine | Theobromine | Phenethylamine | Serotonin |
| Bluecrop | 0.8 | 0 | 0 | 0.009 | 0 |
| Sportan | 4.2 | 0 | 0 | 0.011 | 0 |
| Aurora | 46 | 0 | 0 | 0.389 | 0 |
| Duke | 41 | 0 | 0 | 0.026 | 0 |
| Draper | 36 | 0 | 0 | 0 | 0 |
| Blue Gold 1 | 161 | 0 | 0 | 0 | 0 |
| Blue Gold 2 | 124 | 0 | 0 | 0 | 0 |
| Chandler | 91 | 0 | 0 | 0.027 | 0 |
| Rubel | 76 | 0 | 0 | 0.076 | 0 |
| Liberty | 33 | 0 | 0 | 0 | 0 |
| Reka | 13 | 0 | 0 | 0.039 | 0 |
| Late Blue | 34 | 0 | 0 | 0.646 | 0 |

TABLE 4

Anthocyanin and Anthocyanidin concentrations in different blueberry cultivars.

| Bluberry Cultivar | Extract, in AUC/ml | | Pulp, in AUC/ml | | Total in AUC/ml |
|---|---|---|---|---|---|
| | Anthocyanin, 520 nm | Anthocyanidin, 320 nm | Anthocyanin, 520 nm | Anthocyanidin, 320 nm | |
| Bluecrop | 88,492 | 4,148,264 | 1,528,595 | 21,680 | 5,787,031 |
| Sportan | 529,275 | 6,554,693 | 1,464,605 | 32,175 | 8,580,748 |
| Aurora | 6,539 | 39,305 | 3,916,695 | 416,180 | 4,378,719 |
| Duke | | 7,154 | 2,542,645 | 666,030 | 3215829 |
| Draper | 6,395 | 30,799 | 4,425,325 | 511,940 | 4,974,459 |
| Blue Gold 1 | 10,920 | 64,309 | 6,490,430 | 1,128,345 | 7,694,004 |
| Blue Gold 2 | | 4,391 | 3,965,765 | 447,840 | 4,417,996 |
| Chandler | 1,205,038 | 5,770,768 | 2,107,015 | 312,240 | 9,395,061 |
| Rubel | | 41,824 | 5,950,160 | 980,545 | 6,972,529 |
| Liberty | | 15,509 | 3,920,770 | 1,018,645 | 4,954,924 |
| Reka | | 14,032 | 2,161,550 | 50,640 | 2,226,222 |
| Late Blue | 2,539,354 | 10,092,302 | 4,059,510 | 975,850 | 17,667,016 |

TABLE 5

Catechin and anthocyanin concentrations in different *aronia* cultivars growing in Poland.

| Extracts | Concentration in µg/g | | |
|---|---|---|---|
| | Catechins | Epicatechins | Anthocyanins |
| *Aronia* 1 | 0.93 | 23.76 | 454 |
| *Aronia* 2 | 1.23 | 44.80 | 422 |
| *Aronia* 3 | 1.37 | 68.65 | 418 |
| *Aronia* 4 | 0.67 | 20.62 | 230 |
| *Aronia* 5 | 1.11 | 42.42 | 267 |
| *Aronia* 6 | 1.88 | 42.3 | 103 |
| *Aronia* 7 | 1.84 | 37.35 | 139 |
| *Aronia* 8 | 1.32 | 26.00 | 138 |

Figure 1:
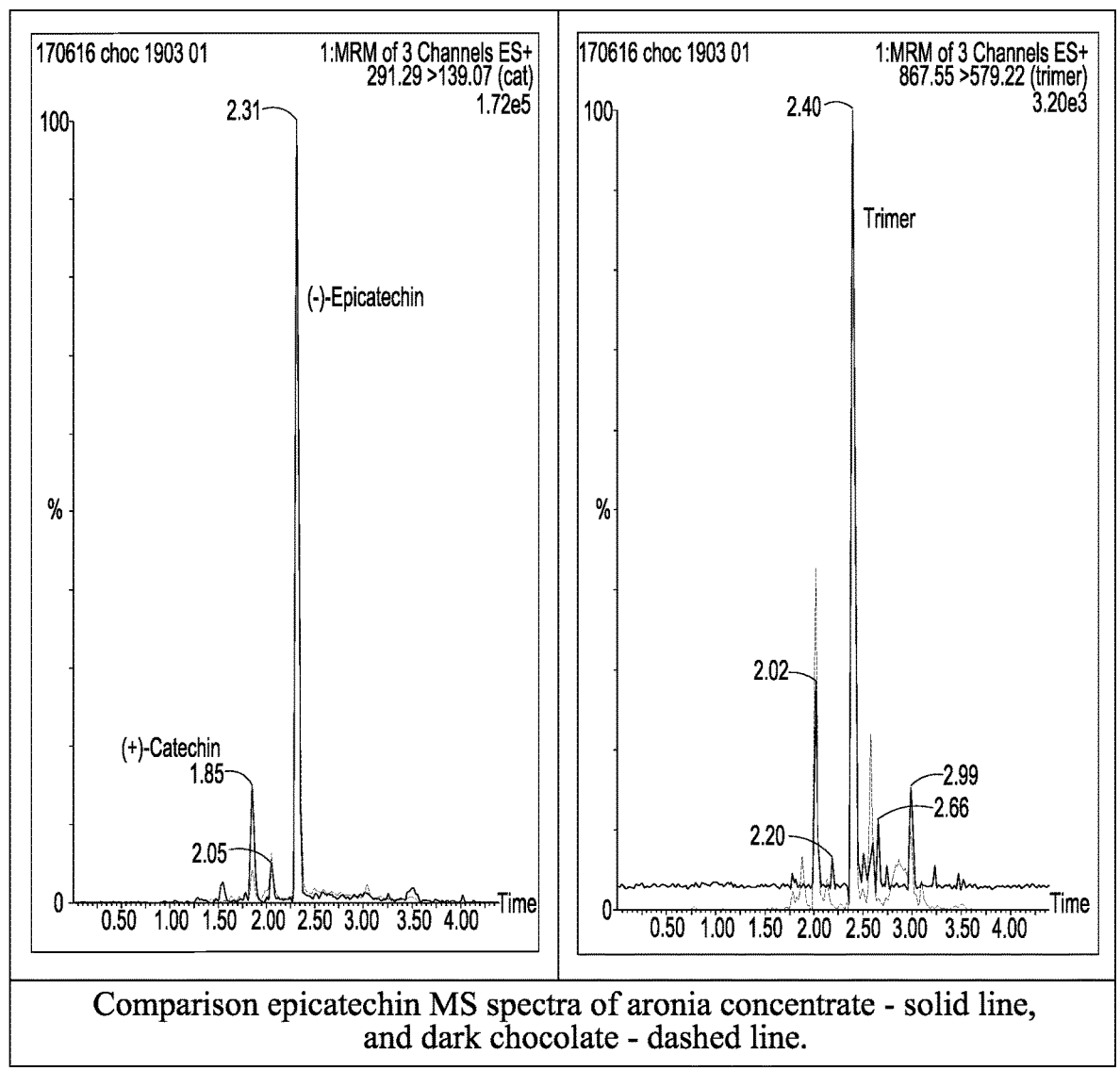
FIG. 1 shows a comparison of the catechin profile of *aronia* and dark chocolate.
Figure 2:
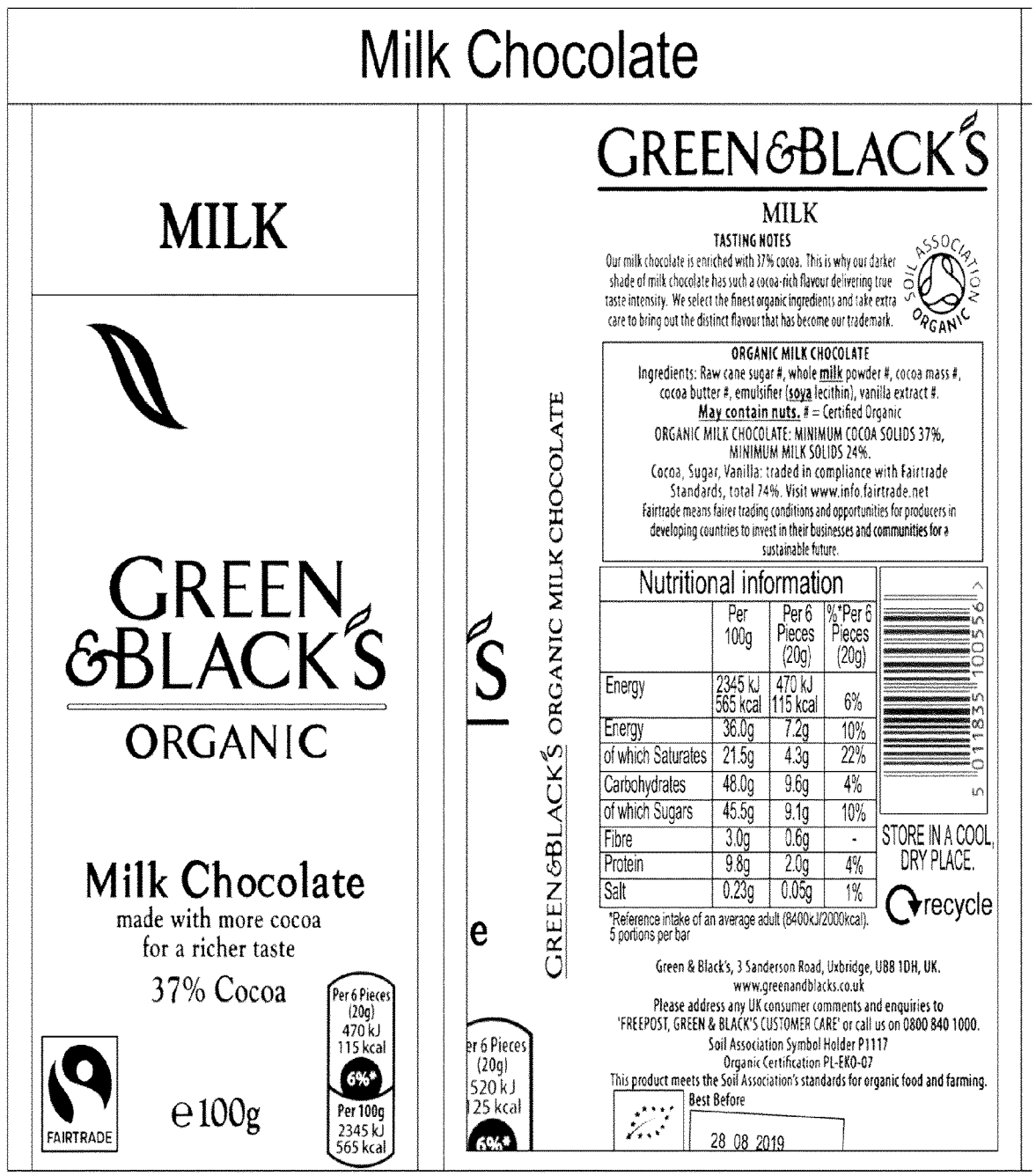
FIG. 2 shows an image of the milk and dark chocolates used as prototypes and their ingredients.
Figure 2:
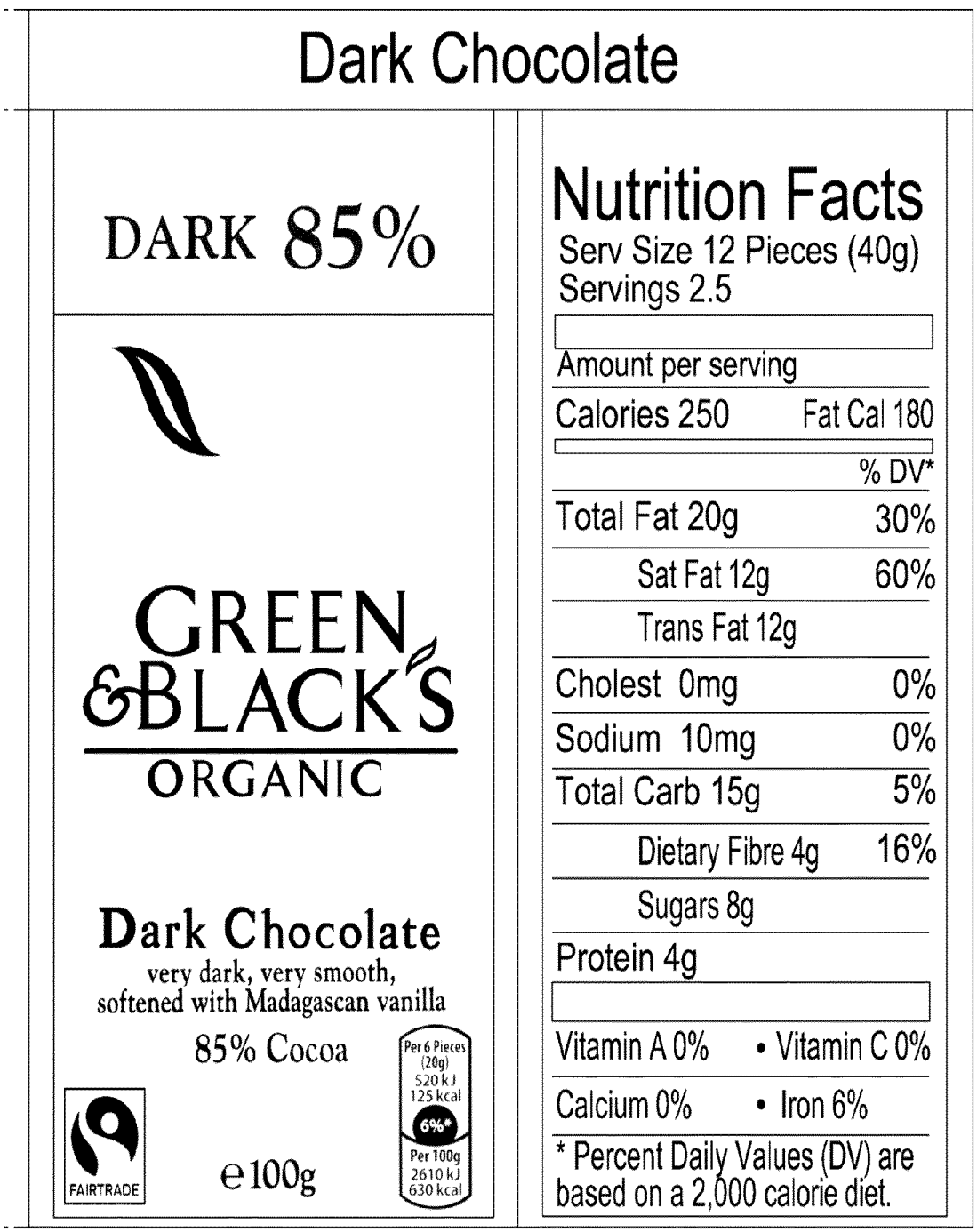

After identification of a suitably rich source of catechins it was important to compare their profile with the cocoa catechins. The comparison of two forms of *aronia* and cocoa catechins, epicatechin and its aggregated trimer, is presented in FIG. 2.

2. Extract Embedment Process and its Verification

To create fortified functional chocolate we used Green & Black, milk, dark (FIG. 3) and white chocolate (illustration not enclosed). Concentrations of catechins and other bioactive health beneficial molecules, in these chocolates are presented in Table 6.

The process of embedment of the extracts into the chocolate was variable and dependent not only on the type of chocolate—milk, dark or white, but also on a number of other specific chocolate parameters, which included but not limited to:

viscosity of the molten chocolate, lecithin, or other emulsifier concentration, tempering protocol, milk protein/fat content, etc.

For verification of the successful embedment of the extracts into chocolate we used our own chocolate sample preparation technique, which was adapted to the specifics of the light microscopy.

TABLE 6

Concentration of catechins, methylxanthines and bioamines in the milk and dark chocolate used.

| | Concentration of Catechins, methylxanthines and bioamines*, in µg/g | | | | | | |
|---|---|---|---|---|---|---|---|
| Product | Catechin | Epicatechin | Dimer B2 | Caffeine | Theobromine | Phenethylamine | Serotonin |
| Milk Chocolate 37% Cocoa | 204 | 646 | 28 | 345 | 1,915 | 2.4 | 3.6 |
| Dark Chocolate 85% Cocoa | 197 | 907 | 287 | 850 | 8,356 | 6.7 | 8.1 |

*Mean of 3 independent measurements

For further experiments we selected extracts from blueberries, bilberries and *aronia*. We made a number of prototypes before we succeeded in obtaining a uniformed distribution, and it was always different for different chocolate matrixes.

In order to create a range of functional milk chocolate we also combined this with co-embedment with other health beneficial molecules, for example carotenoids. Successful embedment was verified by microscopy, examples of which are presented in FIG. 3.

To quantify and standardise the process of embedment in a particular type of chocolate matrix, to guaranty reproducibility in production and potential efficacy it was important to develop a standardised algorithm. This includes specific profiles for different types of chocolate by e.g. quantifying a number of chocolate crystals of different sizes with the embedded particular extract.

An example of such analysis is presented in Table 7.

TABLE 7

Numbers of chocolate crystals of different size with embedded *aronia* polyphenols/anthocyanins (×1000; 30 random fields counted per 1 slide, 3 slides per each product)

| ACC* size | 85% Cocoa Aronia | 85% Cocoa Aronia + Lycopene | 37% Cocoa Aronia | 37% Cocoa Aronia + Lycopene |
|---|---|---|---|---|
| <40 µm | 14.6 ± 3.3 | 11.6 ± 2.7 | 36.0 ± 3.2 | 36.3 ± 3.1 |
| 40-120 µm | 11.3 ± 4.3 | 5.3 ± 2.9 | 9.6 ± 3.3 | 21.6 ± 4.5 |
| >120 µm | 15.0 ± 3.9 | 7.3 ± 3.3 | 6.7 ± 1.5 | Not detected |

**aronia* chocolate crystals*

3. Clinical Validation—Postprandial Study

The first most important study was to establish the impact of our new chocolate products on postprandial glucose levels.

For these purposes we selected an *aronia* extract, and based on it we developed a number of products for this trial:

White Chocolate pieces of 10 g with 500 mg and 1,000 mg of the *aronia* extract,
Milk Chocolate pieces of 10 g with 500 mg of the *aronia* extract,
Milk Chocolate pieces of 10 g with 500 mg of the *aronia* extract and 7 mg lycopene,
Dark Chocolate pieces of 10 g with 500 mg and 1,000 mg the *aronia* extract,
Dark Chocolate pieces of 10 g with 500 mg and 1,000 mg the *aronia* extract and 7 mg lycopene,
Nutella-based spread of 15 g with 500 mg of the *aronia* extract,
Capsules containing 500 mg of *aronia*

This was a crossover clinical study on 6 volunteers of 35-65 years old, 3 women and 3 men. It was a multi-arm trial with one-week interval between each arm. Prior to every experiment volunteers were asked not to consume food, which may contain fruit, vegetable or grain polyphenols and tomato-based products. In the morning of the experiment volunteers were asked to abstain from any food and drink only water.

The serum of the vein blood was analysed. In brief, 10 ml of blood was taken, the serum separated after centrifugation for 10 mins at 3,000 g and then the sample was aliquoted and frozen at −80 C until their analysis.

Firstly, a sample was collected before ingesting of a product, then every hour for 4 hours after ingestion. The results of monitoring of the postprandial glucose level in the blood of these volunteers are presented in the Table 8.

Firstly, they show that ingestion of either dark, or milk or white chocolate resulted in potentially harmful increase in the glucose level reaching 6 mmol/L and above. In addition, ingestion of *aronia* extract capsules also led to significant rise in the postprandial glucose above this safe threshold. This was presumably due to the fact that this extract, like others from berries, are rich with anthocyanins, an integral part of which is different types of sugar.

TABLE 8

Effect of *Aronia* polyphenol-rich extract and chocolate co-crystallisation on postprandial glucose in the crossover clinical trial.

| | | Postprandial blood glucose, in mmol/L | | | | |
|---|---|---|---|---|---|---|
| Product, 10 g | n | baseline | 1 h | 2 h | 3 h | 4 h |
| Milk chocolate, Cocoa 37% control | 6 | 5.2 ± 0.35 | 6.05 ± 0.6 | 5.8 ± 0.5 | 5.6 ± 0.4 | 5.5 ± 0.5 |
| +500 mg *Aronia* capsule* | 6 | 5.35 ± 0.5 | 6.3 ± 0.65 | 6.1 ± 0.6 | 5.75 ± 0.5 | 5.45 ± 0.45 |
| +500 mg *Aronia*** | 6 | 5.3 ± 0.4 | 5.8 ± 0.4 $p < 0.05$ | 5.7 ± 0.5 $p < 0.05$ | 5.5 ± 0.4 | 5.4 ± 0.35 |
| +500 mg *Aronia*** +7 mg Lycopene*** | 6 | 5.2 ± 0.35 | 5.9 ± 0.5 $p < 0.05$ | 5.8 ± 0.5 $p > 0.05$ | 5.6 ± 0.45 $p > 0.05$ | 5.5 ± 0.4 $p > 0.05$ |

TABLE 8-continued

Effect of *Aronia* polyphenol-rich extract and chocolate co-crystallisation on postprandial glucose in the crossover clinical trial.

| Product, 10 g | n | baseline | Postprandial blood glucose, in mmol/L | | | |
|---|---|---|---|---|---|---|
| | | | 1 h | 2 h | 3 h | 4 h |
| Dark chocolate, Cocoa 85% control | 6 | 5.2 ± 0.3 | 6.0 ± 0.55 | 5.7 ± 0.5 | 5.5 ± 0.45 | 5.3 ± 0.35 |
| +500 mg *Aronia* capsule* | 6 | 5.25 ± 0.4 | 6.2 ± 0.6 | 6.0 ± 0.6 | 5.7 ± 0.5 | 5.5 ± 0.55 |
| +500 mg *Aronia*** | 6 | 5.2 ± 0.45 | 5.9 ± 0.5<br>$p > 0.05$ | 5.8 ± 0.55 | 5.6 ± 0.5 | 5.3 ± 0.4 |
| +1,000 mg *Aronia*** | 6 | 5.2 ± 0.45 | 5.75 ± 0.5<br>$p < 0.05$ | 5.55 ± 0.5<br>$p < 0.05$ | 5.45 ± 0.55 | 5.3 ± 0.5 |
| +500 mg *Aronia*<br>+7 mg Lycopene* | 6 | 5.3 ± 0.35 | 5.8 ± 0.4<br>$p < 0.05$ | 5.6 ± 0.45<br>$p > 0.05$ | 5.4 ± 0.4<br>$p > 0.05$ | 5.3 ± 0.35<br>$p > 0.05$ |
| White chocolate | 6 | 5.25 ± 0.4 | 6.2 ± 0.6 | 5.9 ± 0.55 | 5.6 ± 0.5 | 5.4 ± 0.45 |
| +500 mg *Aronia* | 6 | 5.3 ± 0.45 | 5.7 ± 0.45<br>$p < 0.05$ | 5.5 ± 0.35<br>$p < 0.05$ | 5.4 ± 0.4 | 5.2 ± 0.0.35 |
| *Aronia* 500 mg*[1.1.1.1] | 6 | 5.4 ± 0.45 | 6.1 ± 0.55 | 5.9 ± 0.5 | 5.7 ± 0.45 | 5.6 ± 0.5 |
| 1,000 mg**** | 6 | 5.3 ± 0.5 | 6.2 ± 0.5 | 6.0 ± 0.55 | 5.8 ± 0.5 | 5.5 ± 0.55 |

*Aronia* extract in capsule,
**Aronia* embedded concentrate,
***Tomato oleoresin,
****2 *Aronia* extract capsules.

When control chocolate pieces were ingested the extract in a capsule form we observed apparently additive postprandial increase in the glucose level.

However, the main unexpected surprise was observed after ingestion of chocolate samples with the embedded *aronia* extract. There was a slight rise in the postprandial glucose level but it was within the safe health limit (i.e. below 6 mmol/L). The same effect was observed for the products where lycopene was co-embedded with the *aronia* extract too.

The same effect was also observed when instead of *aronia* we used blueberry, or bilberry extract (Table 9).

TABLE 9

Effect of bilberry polyphenol-rich extract and chocolate crystallisation products on postprandial glucose in the crossover clinical trial.

| Product, 10 g | n | baseline | Postprandial blood glucose, in mmol/L | | | |
|---|---|---|---|---|---|---|
| | | | 1 h | 2 h | 3 h | 4 h |
| Dark chocolate, Cocoa 85% control | 6 | 5.2 ± 0.3 | 6.0 ± 0.55<br>$p > 0.05$ | 5.7 ± 0.5<br>$p > 0.05$ | 5.5 ± 0.45<br>$p > 0.05$ | 5.3 ± 0.35<br>$p > 0.05$ |
| +500 mg Bilberry in 1 capsule* | 6 | 5.4 ± 0.5 | 6.2 ± 0.6<br>$p < 0.05$ | 6.0 ± 0.55<br>$p > 0.05$ | 5.85 ± 0.6<br>$p > 0.05$ | 5.6 ± 0.55<br>$p > 0.05$ |
| +500 mg Bilberry** | 6 | 5.3 ± 0.4 | 5.9 ± 0.55<br>$p > 0.05$ | 5.8 ± 0.5<br>$p > 0.05$ | 5.6 ± 0.45<br>$p > 0.05$ | 5.4 ± 0.45<br>$p > 0.05$ |
| +500 mg Bilberry**<br>+4 mg Astaxanthin | 6 | 5.35 ± 0.5 | 5.8 ± 0.55<br>$p > 0.05$ | 5.8 ± 0.5<br>$p > 0.05$ | 5.5 ± 0.5<br>$p > 0.05$ | 5.3 ± 0.45<br>$p > 0.05$ |
| Bilberry 500 mg* | 6 | 5.4 ± 0.45 | 6.1 ± 0.55<br>$p < 0.05$ | 5.9 ± 0.5<br>$p > 0.05$ | 5.7 ± 0.45<br>$p > 0.05$ | 5.6 ± 0.5<br>$p > 0.05$ |

*Bilberry extract in capsule,
**Bilberry embedded concentrate,

The results indicate that lower levels of the postprandial glucose in these new products could be due to the synergetic effect on insulin metabolism and interfere with glucose intestine absorption by not only a combination of cocoa and berry polyphenols, but also by their delivery in a chocolate matrix.

Even more surprising results were observed when chocolate was not a whole product per se but only an ingredient of other consumable products. Nutella is a popular spread where chocolate is only 7.4% of the total mass of the product. When in the crossover study volunteers ingested 15 g of this spread containing 500 mg of *aronia* extract the level of postprandial glucose was noticeably lower than after ingestion of the same amount but unmodified spread, Table 10.

TABLE 10

Effect of ingestion of the Nutella spread with *Aronia* polyphenol clusters on the postprandial glucose in the crossover clinical trial.

| Product, 15 g | n | Postprandial blood glucose, in mmol/L | | | | |
|---|---|---|---|---|---|---|
| | | baseline | 1 h | 2 h | 3 h | 4 h |
| Nutella control* | 6 | 5.5 ± 0.4 | 6.2 ± 0.5 | 6.0 ± 0.55 | 5.7 ± 0.45 | 5.6 ± 0.4 |
| Nutella +500 mg *Aronia* | 6 | 5.5 ± 0.45 | 6.1 ± 0.45 | 5.8 ± 0.4 | 5.6 ± 0.45 | 5.5 ± 0.4 |
| *Aronia* 500 mg** | 6 | 5.4 ± 0.45 | 6.1 ± 0.55 | 5.9 ± 0.5 | 5.7 ± 0.45 | 5.6 ± 0.5 |

*7.4% Cocoa
**Aronia* extract capsule,

These were unexpected results when health-improving properties of a minor, small percent ingredient were translated to the health benefit of the whole consumable product.

4. Clinical Validation—Efficacy Study

Since we established that not only dark but also milk chocolate with embedded *aronia* extract does not have negative impact on the postprandial glucose, it was safe its first efficacy study.

Epicatechins and anthocyanins have well reported anti-oxidant and anti-inflammatory properties. Therefore, the main objective of the study was to assess a possible effect of our products on the level of blood markers of oxidative and inflammatory damage.

For this purpose we recruited 40 people whose blood was positive for the presence of these markers. They were all Caucasians, from 43 to 68 years old, 24 men and 16 women with no serious diseases or adverse conditions. All participants were randomised in 5 groups of 8 people. During the trial we asked all of them not to change their diet and life-style routine.

Each product was administered only once a day and the trial lasted for 4 weeks.

The results of this study demonstrate that both *aronia*-milk and *aronia*-dark chocolate had significantly stronger antioxidant and anti-inflammatory effects than their control chocolates and *aronia* capsules (Tables 11 and 12). It also indicates that we can develop a fortified milk chocolate with antioxidant and anti-inflammatory effects equivalent or even stronger than dark chocolate.

TABLE 11

Changes in the level of inflammatory oxidative damage in the serum of volunteers after administration chocolate-*aronia* polyphenols for 4 weeks.

| Products | n | Serum IOD in MDA μM | | |
|---|---|---|---|---|
| | | 0 weeks | 2 weeks | 4 weeks |
| Milk Chocolate Cocoa 37% control | 8 | 156 ± 16 | 135 ± 14.5<br>Δ = −21 | 127 ± 13.5<br>Δ = −29 |
| Milk Chocolate Cocoa 37% = 500 mg *Aronia** | 8 | 168 ± 15 | 113 ± 12.5<br>Δ = −53 | 79 ± 8.5<br>Δ = −89 |
| Dark Chocolate Cocoa 85% control | 8 | 173 ± 18 | 161 ± 15 (93%)<br>Δ = −12 | 152 ± 16 (88%)<br>Δ = −21<br>p < 0.05 |
| Dark Chocolate Cocoa 85% + 500 mg *Aronia* | 8 | 143 ± 14 | 95 ± 9.5<br>Δ = −48 | 58 ± 6.5<br>Δ = −85 |
| 500 mg *Aronia* | 8 | 183 ± 19 | 180 ± 19<br>Δ = −3 | 177 ± 18.5<br>Δ = −6 |

**Aronia* concentrate,

TABLE 12

Changes in the level of LDL-Px in the serum of volunteers after administration chocolate-*aronia* polyphenols for 4 weeks.

| Products | n | LDL-Px in ELISA × 10³ | |
|---|---|---|---|
| | | 0 weeks | 4 weeks |
| Milk Chocolate Cocoa 37% control | 8 | 670 ± 71 | 629 ± 65<br>Δ = −41 |
| Milk Chocolate Cocoa 37% + 500 mg *Aronia** | 8 | 472 ± 45 | 302 ± 28<br>Δ = −170 |
| Dark Chocolate Cocoa 85% control | 8 | 546 ± 59 | 573 ± 58 |
| Dark Chocolate Cocoa 85% + 500 mg *Aronia* | 8 | 805 ± 86 | 597 ± 62<br>Δ = −208 |
| 500 mg *Aronia* | 8 | 311 ± 62 | 289 ± 32<br>Δ = −22 |

**Aronia* polyphenol concentrate

In addition we studied the potential anti-hypoxia effect of these CAP chocolates and in particular the level of oxygen tissue saturation, $StO_2$. These results are presented in Table 13.

TABLE 13

Changes in the peripheral tissue oxygen saturation $StO_2$ level in volunteers after administration of chocolate - aronia polyphenols for 4 weeks.

| | | $StO_2$ | |
|---|---|---|---|
| Products | n | 0 weeks | 4 weeks |
| Milk Chocolate Cocoa 37% control | 8 | 61.6 ± 6.7 | 63.6 ± 6.5<br>Δ = +2.0, p > 0.05 |
| Milk Chocolate Cocoa 37% + 500 mg Aronia* | 8 | 70.4 ± 7.3 | 74.6 ± 7.8<br>Δ = +4.2, p > 0.05 |
| Dark Chocolate Cocoa 85% control | 8 | 65 ± 7.1 | 70.3 ± 7.4<br>Δ = +5.3, p > 0.05 |
| Dark Chocolate Cocoa 85% + 500 mg Aronia | 8 | 69.6 ± 6.9 | 80.8 ±8.1<br>Δ = +11.2, p < 005 |
| 500 mg Aronia | 8 | 59.4 ± 6.4 | 61.5 ± 6.8<br>Δ = +2.1, p > 0.05 |

*Aronia polyphenol concentrate

These observations could not be explained by simply combining the effects of their "individual components", which would be significantly lower than the performance of the finished products. One plausible explanation of this could be that behind this increased efficacy could be the same synergetic effect, which we observed in the postprandial study above—a combination of coca and berry polyphenols in a chocolate matrix.

One of the main challenges of fortification of chocolate is a fairly quick degradation of molecules or substances newly introduced into it. The main reason behind this is the intrinsic composition of chocolate, which by its nature is a product of microbial and fungal fermentation. It not only has an acidic environment but also active degrading enzymes present there. This in combination creates a rather hostile environment for many newly introduced ingredients, which can lead to their breakdown and inactivation.

5. The Source of t-RSV for Chocolate Fortification

As discussed, fortifying chocolate is extremely challenging. Not only does chocolate have an acidic environment, but it also contains a number of degrading enzymes, creating a hostile environment for any additional ingredient in a chocolate matrix.

To overcome this barrier, a new technology has been developed which can protect t-RSV from degrading factors of not only the chocolate matrix but the human digestive system too. This technology creates a chocolate where t-RSV is protected and which helps to increase its absorption in an unmodified active form.

For this purpose we decided to fortify chocolate with a plant extract that contains a significant and commercially viable level of t-RSV. Although t-RSV is present in raw cocoa in its highest concentration, most of it is lost during the manufacturing process, and in the finished dark chocolate, the resulting level is around 0.09-1.29-2 µg/g Table 14). As a commercial source of resveratrol, raw cocoa has at least two main drawbacks—sustainability of this source and its cost.

To find alternative sources we screened a number of plant extracts. Results are presented in Table 14 and demonstrate that some plants have a significantly higher level of t-RSV, higher even than in red grapes. Among these are such berries as aronia, blueberries, bilberries, cherry morello and barberries, and a grain, buckwheat.

TABLE 14

Comparison of the concentration of trans-Resveratrol in extracts of cocoa products and different plants

| | trans-Resveratrol | |
|---|---|---|
| Products | Literature | Lycotec data |
| Cocoa bean powder West Africa | | >200 µg/g |
| Cocoa nibs or cotyledons | | 46.6 µg/g |
| Dark chocolate Cocoa 70-75% | 0.35-1.85 µg/g | 0.09-1.29-2 µg/g |
| Blueberry | 0.14-0.85 µg/g | |
| Poland | | 34-106 µg/g<br>5.3-9.4 mg/L |
| Czech Republic | | 16.1 µg/g<br>3.5 mg/L |
| Bilberry | 0.71-0.9 µg/g | 36-100 µg/g<br>3.2-5.2 mg/L |
| Aronia | not available | 43-139 µg/g<br>4.8-8.4 mg/L |
| Red wine | 0.2-5.8 mg/L<br>2-7 mg/L | |
| Grape | | |
| Red | | |
| California | 2.5-6.5 µg/g | 7.7 µg/g |
| Chile | | 5.6 µg/g |
| Greece | | 6.0 µg/g |
| Australia | | 1.7 µg/g |
| White | 0-2.9 µg/g | |
| South Africa | | 2.2 µg/g |
| Australia | | 4.9 µg/g |
| Cherry Morello | | 53.2 µg/g |
| Acai | | n/a |
| Barberry | | 64.8 µg/g |
| Goji | | 3.3 µg/g |
| Mulberry | | 10.1 µg/g |
| Sea Buckthorn | | 11.7 µg/g |
| Baobab | | |
| Ghana | | |
| n/i blend | | |
| Malawi | | 0 µg/g |
| Hemp | | 33 µg/g |
| Barley | | 21 µg/g |
| Aubergine | | |
| raw | | 0 µg/g |
| dried | | 9.6 µg/g |
| Flaxseed | | 5 µg/g |
| Buckwheat | | 63 µg/g |

Working with different source, even of same berries, we realised that the concentration of t-RSV was significantly variable not only between different territories, like blueberries from Poland or Czech Republic (Table 14), but even from the cultivar range growing in the same country.

As presented in Table 15, t-RSV in one cultivar of blueberries, like for example Aurora, Late Blue or Blue Gold 2, could be significantly, up to 100 fold, higher than in other varieties of these berries.

TABLE 15

Concentration of trans-Resveratrol in extracts of different blueberry cultivars growing in Poland.

| | | t-RSV concentration | |
|---|---|---|---|
| | Blueberry Cultivar | µg/ml | µg/g dry mass |
| 1 | Bluecrop | 2.2 | 23.7 |
| 2 | Spartan | 0.02 | 0.2 |
| 3 | Chandler | 0 | 0 |
| 4 | Rubel | 0.38 | 2.7 |
| 5 | Blue Gold 2 | 5.28 | 52.3 |

TABLE 15-continued

Concentration of trans-Resveratrol in extracts of
different blueberry cultivars growing in Poland.

|   | Blueberry Cultivar | t-RSV concentration µg/ml | µg/g dry mass |
|---|---|---|---|
| 6 | Duke | 0.76 | 7.2 |
| 7 | Aurora | 9.44 | 106.1 |
| 8 | Liberty | 0.08 | 0.7 |
| 9 | Reka | 0 | 0 |
| 10 | Draper | 0.16 | 1.5 |
| 11 | Blue Gold 1 | 0.54 | 5.3 |
| 12 | Late Blue | 7.68 | 80.0 |

The same diversity was observed for another berry, *Aronia*. Results presented in Table 16 demonstrate up to 10-fold variation in the t-RSV concentration, even between varieties collected within same country, Poland.

TABLE 16

Concentration of trans-Resveratrol in extracts of
different *aronia* varieties growing in Poland.

| Extract | trans-Resveratrol, in µg/g |
|---|---|
| Aronia 1 | 11 |
| Aronia 2 | 48 |
| Aronia 3 | 26 |
| Aronia 4 | 8 |
| Aronia 5 | 84 |
| Aronia 6 | 9.5 |
| Aronia 7 | 13 |
| Aronia 8 | 18 |

6. t-RSV Pharmacokinetics

To assess the pharmacokinetics (PK) of t-RSV of our dark and milk chocolate with embedded bilberry and *aronia* extracts, we undertook a crossover clinical study with the same group of volunteers. On top of these we added into this crossover study a few more groups with Nutella spread where chocolate is only a small ingredient. The design of the study and the sample collection was the same as in the glucose postprandial study described above.

In addition participants consumed two other t-RSV control products, with one-week intervals from each other, —two glasses of red Burgundy wine and 1 capsule of crystalized trans-Resveratrol, 99% purity (Symrise).

Results of this study are presented in the Table 17. They show that 1 mg of t-RSV consumed in the form of red wine resulted in the largest concentration of this molecule in the serum of the blood both in terms of the Area under the Curve (AUC) for the first 4 hours after ingesting, and in its maximum concentration.

When t-RSV was ingested in 100 times higher dose but in a crystallised form its pharmacokinetic parameters were still below the values observed following the consumption of red wine.

There was not much difference in t-RSV serum levels after ingesting either the milk or dark chocolate control samples. Ingestion of the milk chocolate with blueberry extract resulted in the same level of resveratrol as in the control samples.

Ingestion of either white chocolate or Nutella provided no resveratrol detectable in blood.

However, completely unexpected, the level of t-RSV after ingesting milk chocolate with embedded *aronia* extract resulted in about 8 fold increase in the PK of resveratrol (Table 17).

For the dark chocolate the same synergetic boost in the serum concentration of t-RSV was observed after ingesting either blueberry or *aronia* embedded products. In the latter case, the boost was 10 fold, and for the maximum level of resveratrol concentration it reached the same level observed following consumption of red wine.

Ingestion of Nutella spread with *aronia* extract resulted in small but noticeable appearance of t-RSV in the serum of the volunteers.

TABLE 17

Comparison of pharmacokinetics of trans-Resveratrol delivered
in in different products in crossover clinical study.

| | | Pharmacokinetics of t-RSV in human serum | |
|---|---|---|---|
| Product | Amount of ingested t-RSV | AUC 0-4 hours, in ng/ml | Max, in ng/ml |
| Red Wine* | 1 mg | 300-772 | 150-376 |
| t-RSV capsule | 100 mg | 105-380 | 100-207 |
| *Aronia* extract capsule | 29.3 µg | 0 | 0 |
| Nutella** | 0 µg | 0 | 0 |
| Nutella** *Aronia* extract | 34.5 µg | 23 | 16 |
| Milk Chocolate*** | 4.5 µg | 11.5 | 46 |
| Milk Chocolate*** Blueberry extract | 34.5 µg | 8.5 | 13 |
| Milk Chocolate*** *Aronia* extract | 33.8 µg | 83 | 146 |
| Dark Chocolate*** | 0.9 µg | 7.5 | 15 |
| Dark Chocolate** Blueberry extract | 30.9 µg | 60 | 82 |
| Dark Chocolate** *Aronia* extract | 30.2 µg | 108 | 180 |

*350 ml of Burgundy Pinot Noir,
**15 gram,
***10 gram chocolate bar.

This synergy observed was indeed striking. The physical amount of resveratrol, in the form of berry extracts, which was added to the 10 g piece of chocolate was only about 29 or 30 µg. This, in combination with its intrinsic amount present in chocolate would result in the range of 30-35 µg per ingested product. In other words, our products provided the level of bioavailability of trans-Resveratrol comparable with 100 mg of its crystallised form or with two glasses/half bottle of the red Burgundy.

These results demonstrated that the new SIRT chocolate, i.e. the chocolate of the invention, can break the monopoly of red wine as the only significant source of unmodified active t-RSV in human blood.

This invention could be a platform for the development of new functional consumable products which can deliver multiple health benefits of activating not only SIRT proteins but other metabolic targets of resveratrol. If it happens to be of delightful taste then more people can enjoy looking after their health with or without wine.

7. Epicatechin/Catechin Pharmacokinetics

To assess the pharmacokinetics (PK) of epicatechins/ catechin of our milk chocolate with embedded *aronia* extracts, we undertook a crossover clinical study. The number of volunteers was eight in each group of 35 to 66 years old, 4 men and 4 women. The volume of the piece of the ingested chocolate was 10 g per person. The product was ingested with a half glass of warm water in the morning after 12 hours of fasting, and no any other food was taken for the duration of the each arm of the study.

From the results presented in FIG. 6, it can be seen that the combined concentration of the epicatechin metabolites, in terms of the area under the curve, for epicatechin sulphate and O-methylcatechin sulphate, was 2.75 time higher for milk chocolate (cocoa 37% with co-crystallised *aronia* and cocoa polyphenols) than conventional dark chocolate (cocoa 50%).

Results of crossover pharmacokinetic studies of products where chocolate is only a minor ingredient, or not present at all, were pretty unexpected. AUC from 1 hour to 4 hours after ingestion of 1 gram of the *aronia* extract was 0.22 mg/ml of catechin metabolites. When this extract was embedded into Nutella, even at a lower dose of 750 mg, the increase in their AUC was by about 6.8 times higher than in the control extract,

TABLE 18

Crossover *Aronia* catechin metabolite pharmacokinetic studies of chocolate and not chocolate products with embedded clusters of polyphenol-rich *Aronia* extract.

| Product | Pharmacokinetics - epicatechins, ng/ml | | | | | |
|---|---|---|---|---|---|---|
| | 0 h | 1 h | 2 h | 3 h | 4 h | AUC |
| Nutella control* | 0 | 7.92 | 5.24 | 3.54 | 3.11 | 19.81 |
| +750 mg *Aronia** | 0 | 7.62 | 6.58 | 4.07 | 3.04 | 21.31 |
| White chocolate control** | 0 | 0 | 0 | 0 | 0 | 0 |
| +1,000 mg *Aronia*** | 0 | 0.25 | 0.18 | 0.17 | 0.14 | 0.74 |
| *Aronia* 500 mg | 0 | 0.026 | 0.056 | 0.028 | 0.026 | 0.136 |
| 1,000 mg | 0 | 0.042 | 0.079 | 0.054 | 0.045 | 0.220 |

*15 gram,
**10 gram.

8. *Aronia* CyaGal Anthocyanin Pharmacokinetics

CyaGal and CyaAra are the main anthocyanins in *aronia*. To assess their combined pharmacokinetics (PK), after ingestion of some of our products, we used aliquots of the same serum samples, which were collected in the crossover studies above.

Although AUCs for anthocyanins after ingestion of Nutella with *aronia* extract were comparable with the curve after ingestion of *aronia* extract itself, ingestion of fortified white chocolate in particular resulted in more than double and 4 fold increase in the concentration of these molecules in blood, Table 19.

TABLE 19

Crossover of *Aronia* anthocyanins pharmacokinetic studies of chocolate and not chocolate products with embedded clusters of polyphenol-rich *Aronia* extract.

| Product | Pharmacokinetics - anthocyanins, pg/ml | | | | | |
|---|---|---|---|---|---|---|
| | 0 h | 1 h | 2 h | 3 h | 4 h | AUC |
| Nutella control* | 0 | 0 | 0 | 0 | 0 | 0 |
| +750 mg *Aronia** | 0 | 240 | 160 | 90 | 60 | 550 |
| White chocolate control** | 0 | 0 | 0 | 0 | 0 | 0 |
| +1,000 mg *Aronia*** | 0 | 725 | 524 | 244 | 167 | 1,660 |
| *Aronia* 500 mg | 0 | 29 | 59 | 91 | 62 | 241 |
| 1,000 mg | 0 | 45 | 112 | 147 | 100 | 404 |

*15 gram,
**10 gram.

In conclusion, embedment of polyphenol-rich plant extracts into chocolate matrix, or in products where chocolate is even a minor ingredient results in super-additive boost of some polyphenol bioavailability and efficacy. This effect was unexpected, because conventional fortification results in a mere adding of bioactive molecules, without any interaction with each other or with molecules of the food matrix.

REFERENCES

1. Castro-Acosta M L, Lenihan-Geels G N, Corpe C P1, Hall W L. Berries and anthocyanins: promising functional food ingredients with postprandial glycaemia-lowering effects.—Proc Nutr Soc. 2016 August; 75(3):342-55.
2. Park E, Edirisinghe I, Wei H1, Vijayakumar L P, Banaszewski K, Cappozzo J C, Burton-Freeman B. A dose-response evaluation of freeze-dried strawberries independent of fiber content on metabolic indices in abdominally obese individuals with insulin resistance in a randomized, single-blinded, diet-controlled crossover trial.—Mol Nutr Food Res. 2016 May; 60(5):1099-109.
3. Li D1, Zhang Y2, Liu Y1, Sun R1, Xia M3. Purified anthocyanin supplementation reduces dyslipidemia, enhances antioxidant capacity, and prevents insulin resistance in diabetic patients.—J Nutr. 2015 April; 145(4): 742-8.
4. Ramirez-Sanchez 11, Taub P R, Ciaraldi T P, Nogueira L, Coe T, Perkins G, Hogan M, Maisel A S, Henry R R, Ceballos G, Villarreal F. (−)-Epicatechin rich cocoa mediated modulation of oxidative stress regulators in skeletal muscle of heart failure and type 2 diabetes patients.—Int J Cardiol. 2013 Oct. 9; 168(4):3982-90.
5. Dorenkott M R, Griffin L E, Goodrich K M, Thompson-Witrick K A, Fundaro G, Ye L, Stevens J R, Ali M, O'Keefe S F, Hulver M W, Neilson A P. Oligomeric cocoa procyanidins possess enhanced bioactivity compared to monomeric and polymeric cocoa procyanidins for preventing the development of obesity, insulin resistance, and impaired glucose tolerance during high-fat feeding.—J Agric Food Chem. 2014 Mar. 12; 62(10):2216-27.
6. Chamira Dilanka Fernando and Preethi Soysa; Extraction Kinetics of phytochemicals and antioxidant activity during black tea. (*Camellia sinensis* L.) brewing. Fernando and Soysa Nutrition Journal (2015) 14:74.
7. Ivan M. Petyaev, Dmitry Pristenskiy, Tatyana Bandaletova, Natalia E. Chalyk, Victor Klochkov, Nigel H. Kyle. Lycosome Formulation of Dark Chocolate Increases Absorption Cocoa Catechins and Augments Their Anti-Inflammatory and Antioxidant Properties. American Journal of Food Science and Nutrition. (2016) 3(3): 37-44.
8. Anghel Brito, Carlos Areche, Beatriz Sepúlveda, Edward J. Kennelly and Mario J. Simirgiotis; Anthocyanin Characterization, Total Phenolic Quantification and Antioxidant Features of Some Chilean Edible Berry Extracts. Molecules 2014, 19, 10936-10955;
9. YUKO NAKAMURA, HITOSHI MATSUMOTO, MASASHI MORIFUJI, HIROYUKI IIDA, AND YASUO TAKEUCHI; Development and Validation of a Liquid Chromatography Tandem Mass Spectrometry Method for Simultaneous Determination of Four Anthocyanins in Human Plasma after Black Currant Anthocyanins Ingestion. J. Agric. Food Chem. 2010, 58, 1174-1179.
10. Ivan M. Petyaev, Valeriy V. Tsibezov; ANTIBODY SPECIFIC FOR TRANS-RESVERATROL AND USE THEREOF. Patent Application WO2013068758 A1, PCT/GB2012/052790, publication 16 May 2013, priority date 11 Nov. 2011.
11. Postprandial Blood Glucose. American Diabetes Association. (2001) Diabetes Care, v. 24, No. 4, 775-778.
12. Johnston Kelly, Sharp Paul, Clifford Michael and Morgan Linda (2005), Dietary polyphenols decrease glucose uptake by human intestinal Caco-2 cells, FEBS Letters, 579, doi: 10.1016/j.febslet.2004.12.099.
13. Dolinsky V W, Dyck J R. Calorie restriction and resveratrol in cardiovascular health and disease. Biochim Biophys Acta. 2011 November; 1812(11):1477-89.
14. Bonnefont-Rousselot D. Resveratrol and Cardiovascular Diseases. Nutrients. 2016 May 2; 8(5).
15. Bavaresco L, Lucini L, Busconi M3, Flamini R, De Rosso M. Wine Resveratrol: From the Ground Up. Nutrients. 2016 Apr. 14; 8(4):222.

The invention claimed is:

1. A consumable chocolate product comprising:
   one or more cocoa bean products;
   between 1 and 20% of a polyphenol-rich plant extract by weight of the total product; and
   clusters of polyphenol-cocoa bean product crystals;
   wherein the polyphenol-rich plant extract is a hydrogel derived from a berry, wherein the berry is selected from the group consisting of *aronia*, chokeberries, rowanberries, bilberries, blueberries, cranberries, blackcurrants, redcurrants, cherries, acai, barber, sea buckthorn and blackberries.

2. The consumable chocolate product of claim 1, wherein said cocoa bean product comprises between 10 and 50%, cocoa butter and/or cocoa solid and said consumable product comprises between 3 and 10% polyphenol-rich plant extract, by weight of the total product.

3. The consumable chocolate product of claim 1, wherein said consumable product comprises between 4 and 16% polyphenol-rich plant extract by weight of the total product and wherein said cocoa bean product comprises at least 50% cocoa butter and/or cocoa solid.

4. The consumable chocolate product of claim 1 wherein the consumable product is a spread, paste, cream, confectionary or bakery product, health bar or other health consumable product.

5. The consumable chocolate product of claim 1, wherein the polyphenol is selected from the group consisting of stilbenoids, catechins, epicatechins, gallocatechins, anthocyanins, anthocyanidins, curcumin, flavones, flavanols, flavanones, isoflavones, chalcones, phenolic acids and lignans.

6. The consumable chocolate product of claim 5, wherein the stilbenoid is resveratrol.

7. The consumable chocolate product of claim 6, wherein the resveratrol is trans-resveratrol (t-RSV).

8. The consumable chocolate product of claim 1, wherein the consumable product further comprises one or more additional agents selected from the group consisting of carotenoids, essential fatty acids, vitamins, whey protein or peptides, amino acids, and minerals.

9. The consumable chocolate product of claim 8, wherein the carotenoid is lycopene and wherein the consumable product comprises between 0.05 and 0.10% lycopene.

10. The consumable chocolate product of claim 9, wherein the carotenoid is lycopene and wherein the consumable product comprises 0.07% lycopene.

11. The consumable chocolate product of claim 1 being devoid of cocoa butter.

12. A consumable chocolate product comprising one or more cocoa bean products and a polyphenol-rich plant extract, wherein said product comprises polyphenol-cocoa bean product crystal clusters, wherein said plant extract is an *aronia* extract.

13. The consumable chocolate product of claim 12, wherein said product comprises at least 50% small clusters, and/or up to 20% large clusters of polyphenol-cocoa bean product crystals.

* * * * *